US 7,041,449 B2

(12) United States Patent
Prolla et al.

(10) Patent No.: US 7,041,449 B2
(45) Date of Patent: May 9, 2006

(54) METHODS OF SCREENING FOR COMPOUNDS THAT INHIBIT EXPRESSION OF BIOMARKER SEQUENCES DIFFERENTIALLY EXPRESSED WITH AGE IN MICE

(75) Inventors: Tomas A. Prolla, Madison, WI (US); Richard H. Weindruch, Madison, WI (US); Cheol-Koo Lee, Madison, WI (US); Tsuyoshi Kayo, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 495 days.

(21) Appl. No.: 10/098,205

(22) Filed: Mar. 15, 2002

(65) Prior Publication Data

US 2003/0032030 A1 Feb. 13, 2003

Related U.S. Application Data

(60) Provisional application No. 60/277,382, filed on Mar. 19, 2001.

(51) Int. Cl.
*C12Q 1/68* (2006.01)
*C12P 19/34* (2006.01)
*C07H 21/02* (2006.01)
*C07H 21/04* (2006.01)

(52) U.S. Cl. .............................. 435/6; 435/7.1; 435/29; 435/91.2; 536/23.1; 536/23.5

(58) Field of Classification Search .................... 435/6, 435/7.1, 91.2, 4, 29; 536/23.1, 23.5; 800/3; 424/9.1, 9.2
See application file for complete search history.

(56) References Cited

U.S. PATENT DOCUMENTS

| 6,329,209 B1 * | 12/2001 | Wagner et al. ............... 436/518 |
| 6,569,624 B1 * | 5/2003 | Weindruch et al. ............ 435/6 |
| 2001/0016332 A1 | 8/2001 | Ruvkun et al. |
| 2002/0102553 A1 | 8/2002 | Coleman et al. |
| 2003/0157526 A1 | 8/2003 | Weindruch et al. |

OTHER PUBLICATIONS

Lee et al. Nature. Jul. 2000. 25: 294-297.*
Zhang et al. Kidney International. 1999. 56: 549-558.*
Welle et al. Physiol Genomics. 2003. 14: 149-159.*
Weindruch et al. Mechanisms of Ageing and Development. 2002. 123: 177-193.*
Butler et al. Journal of Gerontology. 2004. 59A:560-567.*
McCarroll et al. Nature Genetics. 2004. 36: 197-204.*

* cited by examiner

*Primary Examiner*—Carla J. Myers
(74) *Attorney, Agent, or Firm*—Quarles & Brady LLP

(57) ABSTRACT

A method of measuring the biological age of a multicellular organism is disclosed. In one embodiment, the method comprises the steps of: (a) obtaining a sample of nucleic acid isolated from the organism's organ, tissue or cell, wherein the nucleic acid is RNA or a cDNA copy of RNA and (b) determining the gene expression pattern of at least one of the genes selected from the group consisting of M21050, Z49204, U49430, K02782, X58861, X66295, M22531, X67809, U19118, M64086, M63695, U39066, X92590, X56518, AA182189, X16493, U20344, X16834, X82648, D00754, D16313, L38971 and X15789.

5 Claims, 8 Drawing Sheets

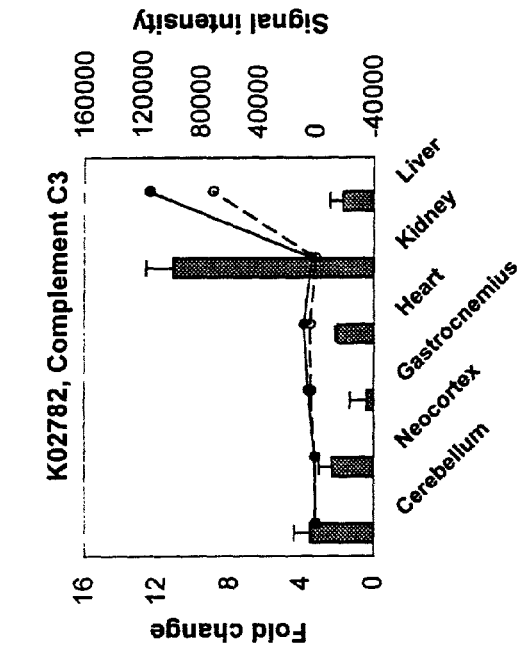
FIG. 3
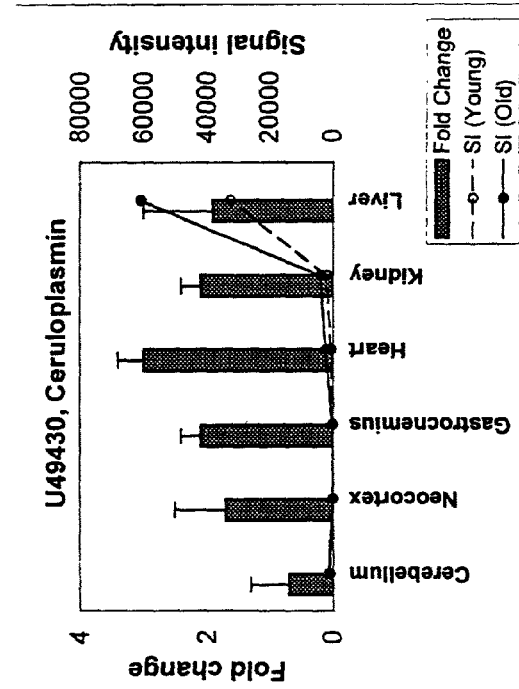
FIG. 5
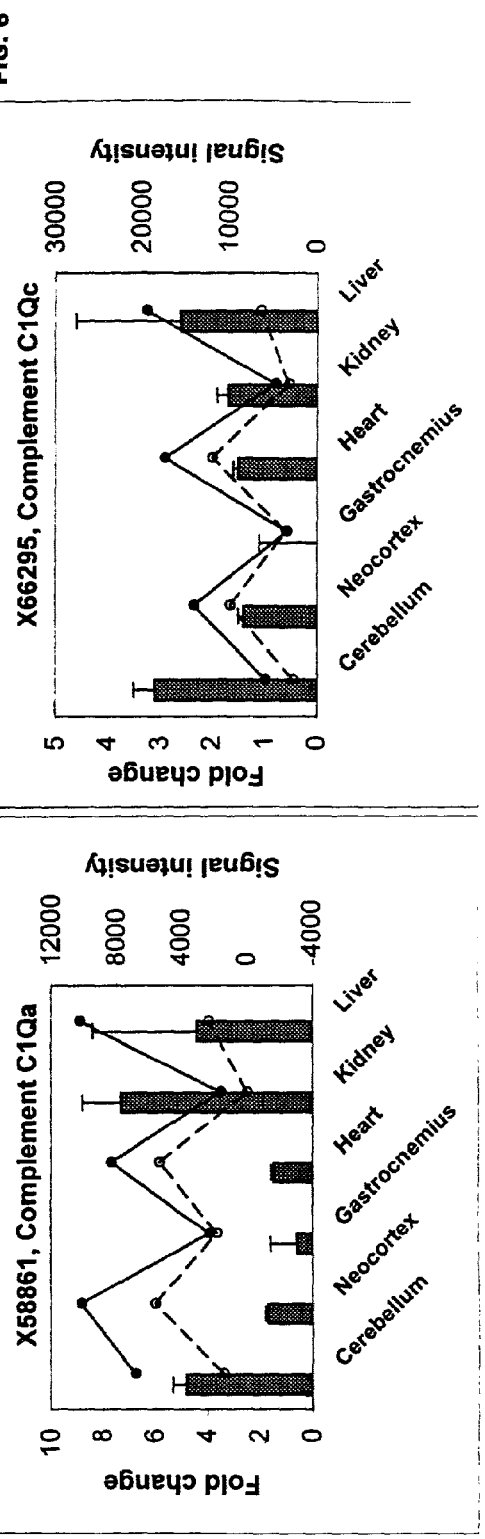
FIG. 4
FIG. 6

Up in 5 of 6 Tissues

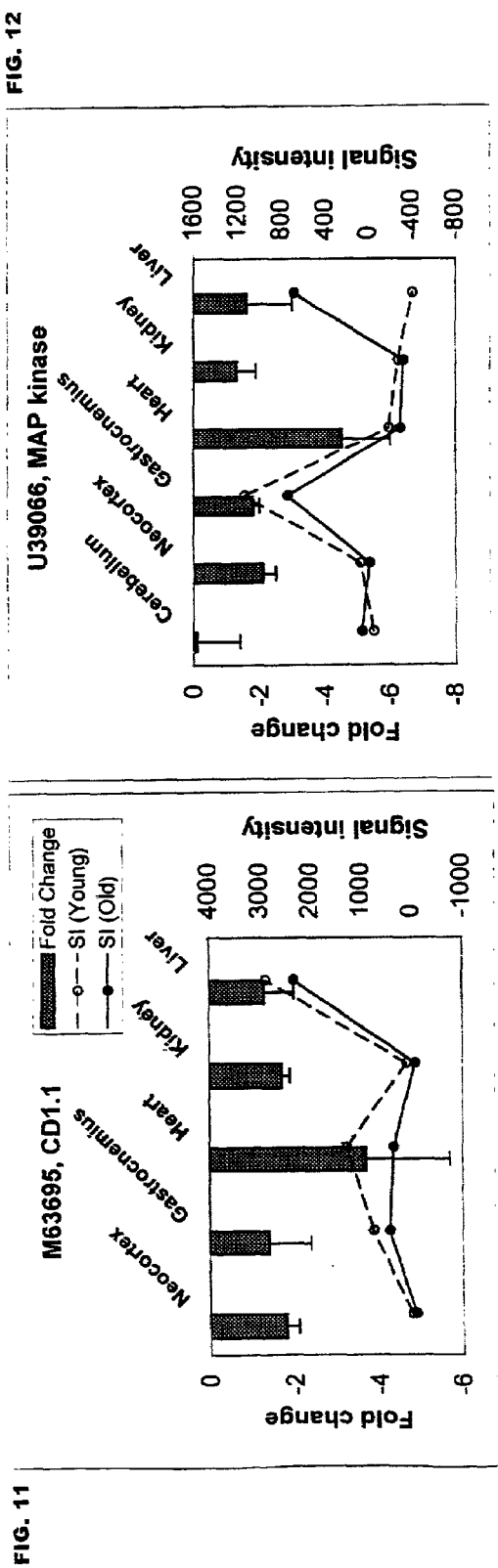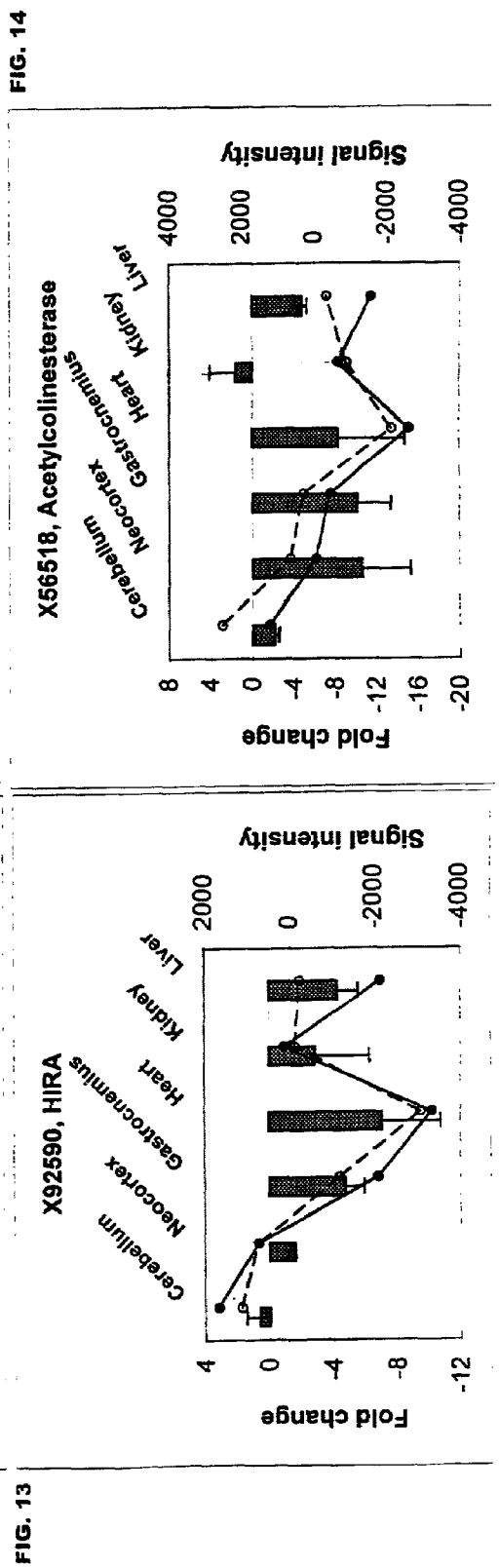

Down in 5 of 6 Tissues

Up in 4 Postmitotic Tissues

Down in 4 Postmitotic Tissues
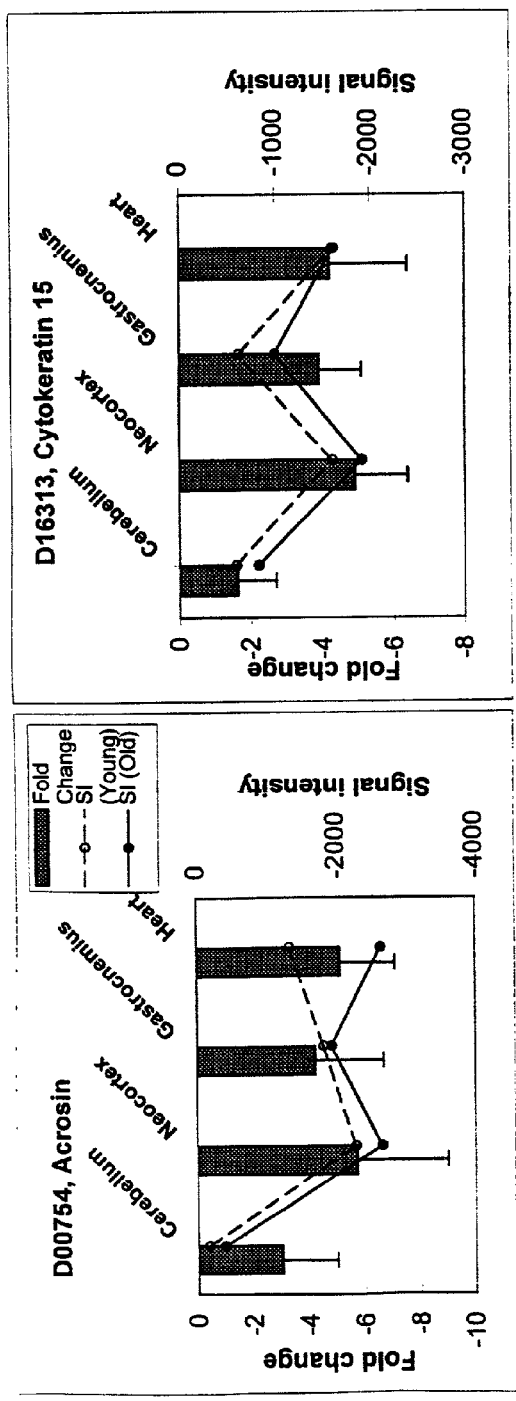
FIG. 22
FIG. 21
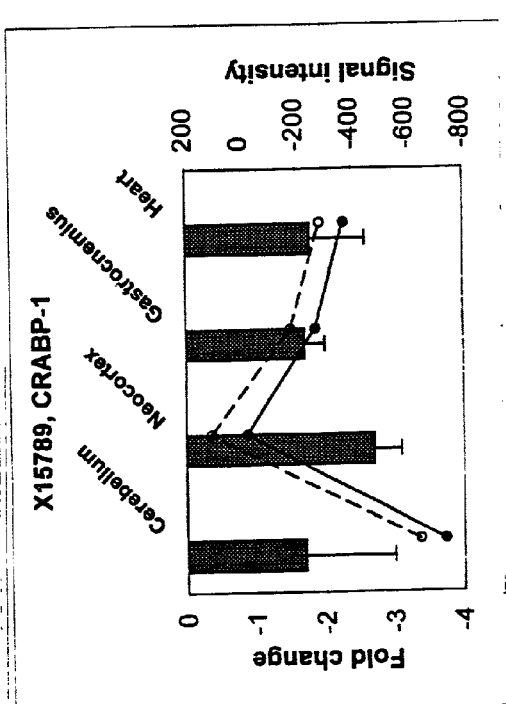
FIG. 23

SEQUENCE LISTING

<160> NUMBER OF SEQ ID NOS: 5

<210> SEQ ID NO 1
<211> LENGTH: 889
<212> TYPE: DNA
<213> ORGANISM: Mus musculus
<300> PUBLICATION INFORMATION:
<308> DATABASE ACCESSION NUMBER: GenBank/M21050
<309> DATABASE ENTRY DATE: 1994-10-04
<313> RELEVANT RESIDUES: (1)..(889)

<400> SEQUENCE: 1

```
catttaaccc catgtctctt tcctccacag ggtggcatgg cgagcacact gtcaaaaccg      60
agatctgtcc cagtatattc ggaactgcgg agtctgaccg cggtgtgctt ctactgcagc     120
tcattcggtc tctttctcac tgtaggagta gatatgagag aggtcacatt ccctcgattt     180
cccctctaag tcacaggact tcagcagaaa cagggcaaaa cagagacttc ctcctcacaa     240
gcttcagctg atgctgtgtt gtgcaaagtc tcccttgtca gtcagcacag ccctggacgc     300
tggtgacagt cagccaacac aatgatcacc acacagacac ctctgtaggt cagttcttca     360
gccaggaagt gattcacatt gagttccatt ggaattcatc ttaatcagac ctgtgtgaat     420
aaaaatacaa gaactgctta taggagacca gttgatcttg ggaaacagca gtcgtgtgag     480
ctgcagggct ttgtgcagtc ccagcaccca gttagaacag cctctgtggt gggccgggaa     540
ggtttctgag ggcacaggag tctcagtgga tgagaactga gattgtctga actcagaaac     600
ttatcaggga acccgtgacc tgtctttctt agagctgccc ctttcatctt gcttaaaaaa     660
taaattctca gctcatgtgt cagtctgttt aacccttgag aggatgttcc cagtgtcacg     720
aggcattcag gagcgactag tgagctgtgc ctgtcctgat cttcttaag ttccttcatt     780
cacactaact ctgagacaga tgagcctgta tcagcaaata accacaggag caaatctaat     840
ctcatagtga aaaagtacaa atggcattaa atcattttca atgcacagg                889
```

<210> SEQ ID NO 2
<211> LENGTH: 3363
<212> TYPE: DNA
<213> ORGANISM: Mus musculus
<300> PUBLICATION INFORMATION:
<308> DATABASE ACCESSION NUMBER: GenBank/U49430
<309> DATABASE ENTRY DATE: 1996-09-12
<313> RELEVANT RESIDUES: (1)..(3363)

<400> SEQUENCE: 2

```
ttttgcaaca ttaaattgtg tcagccaagc aaatgcagcc ctatttataa aattgcttgc         60
ttctggtttc actttattgc atcgtgggct ccgagaggga gaaaaatgaa gtttttgctg        120
cttagcacat ttatattttt gtatagttcc ttagccttgg caagagataa gcattatttc        180
attggaatta ctgaagcagt atgggactat gcttctggca ctgaagaaaa gaaacttatt        240
tcagttgaca cggaacagtc caatttctat cttcaaaatg gtccagatcg tattggaagg        300
aaatataaga aggccccttta ttttgagtac acagatggca cctttagtaa gactatagac        360
aaaccagcct ggctagggtt tttaggccct gtcatcaaag ctgaagttga agataaagtt        420
tatgttcact aaagaaccct tgcctctagg atctacactt tcatgcaca tggggtaacg        480
tacaccaagg agtatgaggg agccgtctac cctgataaca ccactgattt tcaacgggct        540
gatgacaaag tgcttcccgg acaacagtat gtgtatgtgc tgcatgccaa tgagccaagt        600
cctggagagg gagacagcaa ttgtgtgacc aggatttacc actcccatgt tgatgctcca        660
aaagatattg catcaggact cataggacct ctaatactct gtaaaaaagg ttctctatat        720
aaggaaaaag agaaaaatat tgaccaagaa tttgtactaa tgttctctgt ggtggatgaa        780
aatctcagct ggtatctgga agataacatc aaaaccttct gctctgaacc cgagaaagtt        840
gataaagaca atgaagactt ccaggaaagc aacaggatgt actctataaa tggatataca        900
tttggaagcc tcccagggct ctcgatgtgt gcagcagaca gagtgaagtg gtacctttt         960
ggtatgggta atgaagttga tgtgcattca gctttctttc atggccaagc cctgaccagc       1020
aggaactatc aaaccgatat aatcaacctg ttccctgcca ccctaattga tgcttatatg       1080
gtggcccaga atcctggagt ctggatgctc agttgccaga acctaaacca tctgaaagct       1140
gggttgcaag ccttttttcca ggtccaggac tgtaacaagc cttcatcaaa ggataatatc       1200
cgtgggaagc atgttagaca ctattacatt gctgccgagg aagtcatctg gaattatgct       1260
ccctctggta tagacatctt cactgaagaa aaattaacag cctctggaag tgattcaggg       1320
gtatttttg agcaaggtgc cacaagaatt ggtggctctt ataaaaaaat ggcatatcgt       1380
gagtacacag atggttcctt cacaaaccga aagagagag gccctgatga ggaacatctt       1440
ggaatcctag gtcctgtcat tgggcagaa gtaggagaca ccattaaagt caccttttcat       1500
aacaaaggac agcatcatct cagcattcag ccaatgggag taagtttcac tgcagaaaat       1560
gagggaacat actatggccc accaggtgcg tcctcacagc aagcagcctc ccatgtggct       1620
cccaaahaaa cctttacata cgaatggact gtccccaaag aaatgggacc cacttatgca       1680
gatcctgtgt gcctatctaa gatgtactac tctgccgttg accccaccaa agatatattt       1740
actgggctta ttgggccaat gaaaatatgc aagaaaggca gcttacttgc tgatgggaga       1800
cagaaagatg tagacaaaga gttctacttg tttcccacag tgtttgatga aatgagagt        1860
ttactcttag atgataatat caggatgttc acacatgcac ctgatcaggt ggataaggaa       1920
gatgaagact tcaggagtc taataagatg cactccatga atgggttcat gtatggcaat       1980
cagtcctggc tcatatgtgt tctaggagaa tccatcgtgt ggtatttgtt cagcgctgga       2040
aatgaggctg atgtgcatgg gatatacttt tcaggaaata cttatctgtg taaaggagaa       2100
gagagagaca ctgcaaaccct attccctcat aaaagtctca cccttctcat gaaccctgac       2160
acaaaaggga cttttgatgt tgagtgcctt acaacggatc actacacagg tggcatgaag       2220
caaaaataca ctgtgaacca gtgccagcgg cagtttgaag atttcactgt ctaccttgga       2280
```

-continued

```
gaaaggacct actatgtgga cgccgtagag gtggaatggg attactcacc aagcagggcc     2340
tgggaaaagg agctgcatca tttgcaagag caaaatgttt caaatgtatt tttggataaa     2400
gaagagtttt tcataggctc aaagtacaag aaggttgtgt atcgccagtt tactgacagc     2460
tcattcagag aacaggtgaa gagacgagcc gaagaagacg agcacttggg catccttggc     2520
ccaccaattc atgcaaatgt tggagacaaa gttaaagttg tctttaaaaa tatggcaacc     2580
aggccatatt caatacatgc ccatggggtg aaaacagaga gttctacagt tgttccaacg     2640
ttaccaggtg aagttgcaac ttatacatgg caaattccag aaagatcagg ggctggaaga     2700
gaggattcag cttgtatccc atgggcttat tactcaactg tggatcgagt taaggacctc     2760
tatagtgggc taataggccc attgattgtt tgtcggaagt cttatgtgaa agtattcagt     2820
cctaaaaaga aatggagtt tttccttctg tttctagtat ttgatgagaa tgaatcttgg     2880
tacttagatg ataacatcaa aacatactct gaacaccctg agaaagtaaa caaagacaac     2940
gaggaattcc tagaaagcaa taaaatgcat gctattaatg ggaaaatgtt tggaaaccta     3000
caaggcctca caatgcacgt gaaagatgaa gtcaactggt atctgatggg aatgggcaat     3060
gaaatagacc tgcacactgt acacttccac ggccacagct ccaatacaa gcacagggga     3120 gtatacagtt ctgatgtctt tgaccttttc cctggaacat accaaacctt agaaatgttt     3180
ccccaaacac ctggaacctg gttactccac tgccacgtga ctgaccatgt ccatgctggg     3240
atggcaacta cctacactgt tttaccagta gaacaagaga ctaagtctgg ctgaatgaaa     3300
taaattggcg ataagtggaa aacgagaaca atgagtcatt tcaaacattt caaaaaaaac     3360
tcg                                                                   3363
```

<210> SEQ ID NO 3
<211> LENGTH: 5087
<212> TYPE: DNA
<213> ORGANISM: Mus musculus
<300> PUBLICATION INFORMATION:
<308> DATABASE ACCESSION NUMBER: GenBank/K02782
<309> DATABASE ENTRY DATE: 1998-09-23
<313> RELEVANT RESIDUES: (1)..(5087)

<400> SEQUENCE: 3

```
gcctctgccc acccctgccc cttacccctt cattccttcc acctttttcc ttcactatgg       60
gaccagcttc agggtcccag ctactagtgc tactgctgct gttggccagc tccccattag      120
ctctggggat ccccatgtat tccatcatta ctcccaatgt cctacggctg gagagcgaag      180
agaccatcgt actggaggcc cacgatgctc agggtgacat cccagtcaca gtcactgtgc      240
aagacttcct aaagaggcaa gtgctgacca gtgagaagac agtgttgaca ggagccagtg      300
gacatctgag aagcgtctcc atcaagattc cagccagtaa ggaattcaac tcagataagg      360
aggggcacaa gtacgtgaca gtggtggcaa acttcgggga acggtggtg agaaagcag       420 tgatggtaag cttccagagt gggtacctct catccagac agacaagacc atctacaccc      480
ctggctccac tgtcttatat cggatcttca ctgtggacaa caacctactg cccgtgggca      540
agacagtcgt catcctcatt gagacccccg atggcattcc tgtcaagaga gacattctgt      600
cttccaacaa ccaacacggc atcttgcctt tgtcttggaa cattcctgaa ctggtcaaca      660 tgggcagtg aagatccga gccttttacg aacatgcgcc gaagcagatc ttctccgcag      720
agtttgaggt gaaggaatac gtgctgccca gttttgaggt ccgggtggag cccacagaga      780 catttttatta tcgatgac ccaaatggcc tggaagtttc catcatagcc aagttcctgt       840 acgggaaaaaa cgtggacggg acagccttcg tgatttttgg ggtccaggat ggcgataaga      900
```

```
agatttctct ggcccactcc ctcacgcgcg tagtgattga ggatggtgtg ggggatgcag      960
tgctgacccg gaaggtgctg atggaggggg tacggccttc caacgccgac gccctggtgg     1020
ggaagtccct gtatgtctcc gtcactgtca tcctgcactc aggtagtgac atggtagagg     1080
cagagcgcag tgggatcccg attgtcactt ccccgtacca gatccacttc accaagacac     1140
ccaaattctt caagccagcc atgccctttg acctcatggt gttcgtgacc aaccccgatg     1200
gctctccggc cagcaaagtg ctggtggtca ctcagggatc taatgcaaag gctctcaccc     1260
aagatgatgg cgtggccaag ctaagcatca acacacccaa cagccgccaa ccccctgacca     1320
tcacagtccg caccaagaag gacactctcc cagaatcacg gcaggccacc aagacaatgg     1380
aggcccatcc ctacagcact atgcacaact ccaacaacta cctacacttg tcagtgtcac     1440
gaatggagct caagccgggg gacaacctca atgtcaactt ccacctgcgc acagacccag     1500
gccatgaggc caagatccga tactacacct acctggttat gaacaagggg aagctcctga     1560
aggcaggccg ccaggttcgg gagcctggcc aggacctggt ggtcttgtcc ctgcccatca     1620
ctccagagtt tattccttca tttcgcctgg tggcttacta cacctgatt ggagctagtg      1680
gccagaggga ggtggtggct gactctgtgt gggtggatgt gaaggattcc tgtattggca     1740
cgctggtggt gaagggtgac ccaagagata accatctcgc acctgggcaa caaacgacac     1800
tcaggattga aggaaaccag ggggcccgag tggggctagt ggctgtggac aagggagtgt     1860
ttgtgctgaa caagaagaac aaactcacac agagcaagat ctgggatgtg gtagagaagg     1920
cagacattgg ctgcaccca ggcagtggga agaactatgc tggtgtcttc atggatgcag      1980
gcctggcctt caagacaagc caaggactgc agactgaaca gagagcagat cttgagtgca     2040
ccaagccagc agcccgccgc cgtcgctcag tacagttgat ggaaagaagg atggacaaag     2100
ctggtcagta cactgacaag ggtcttcgga agtgttgtga ggatggtatg cgggatatcc     2160
ctatgagata cagctgccag cgccgggcac gcctcatcac ccagggcgag aactgcataa     2220
aggccttcat agactgctgc aaccacatca ccaagctgcg tgaacaacac agaagagacc     2280
acgtgctggg cctggccagg agtgaattgg aggaagacat aattccagaa gaagatatta     2340
tctctagaag ccacttccca cagagctggt tgtggaccat agaagagttg aaagaaccag     2400
agaaaaatgg aatctctacg aaggtcatga acatctttct caaagattcc atcaccacct     2460
gggagattct ggcagtgagc ttgtcagaca agaaagggat ctgtgtggca gacccctatg     2520
agatcagagt gatgcaggac ttcttcattg acctgcggct gccctactct gtagtgcgca     2580
acgaacaggt ggagatcaga gctgtgctct tcaactaccg tgaacagcag gaacttaagg     2640
tgagggtgga actgttgcat aatccagcct tctgcagcat ggccaccgcc aagaatcgct     2700
acttccagac catcaaaatc cctcccaagt cctcgtggc tgtaccgtat gtcattgtcc      2760
ccttgaagat cggccaacaa gaggtggagg tcaaggctgc tgtcttcaat cacttcatca     2820
gtgatggtgt caagaagaca ctgaaggtcg tgccagaagg aatgagaatc aacaaaactg     2880
tggccatcca tactggac ccagagaagc tcggtcaagg gggagtgcag aaggtggatg        2940
tgcctgccgc agaccttagc gaccaagtgc cagacacaga ctctgagacc agaattatcc     3000
tgcaagggag cccggtggtt cagatggctg aagatgctgt ggacggggag cggctgaaac     3060
acctgatcgt gaccccgca ggctgtgggg aacagaacat gattggcatg acaccaacag      3120
tcattgcggt acactacctg gaccagaccg aacagtggga gaagttcggc atagagaaga     3180
ggcaagaggc cctggagctc atcaagaaag ggtacaccca gcagctggcc ttcaaacagc     3240
```

```
ccagctctgc ctatgctgcc ttcaacaacc ggcccccccag cacctggctg acagcctacg    3300
tggtcaaggt cttctctcta gctgccaacc tcatcgccat cgactctcac gtcctgtgtg    3360
gggctgttaa atggttgatt ctggagaaac agaagccgga tggtgtcttt caggaggatg    3420
ggcccgtgat tcaccaagaa atgattggtg gcttccggaa cgccaaggag gcagatgtgt    3480
cactcacagc cttcgtcctc atcgcactgc aggaagccag ggacatctgt gaggggcagg    3540
tcaatagcct tcctgggagc atcaacaagg caggggagta tattgaagcc agttacatga    3600
acctgcagag accatacaca gtggccattg ctgggtatgc cctggccctg atgaacaaac    3660
tggaggaacc ttacctcggc aagtttctga acacagccaa agatcggaac cgctgggagg    3720
agcctgacca gcagctctac aacgtagagg ccacatccta cgccctcctg gccctgctgc    3780
tgctgaaaga ctttgactct gtgccccctg tagtgcgctg gctcaatgag caaagatact    3840
acggaggcgg ctatggctcc acccaggcta ccttcatggt attccaagcc ttggcccaat    3900
atcaaacaga tgtccctgac cataaggact gaacatgga tgtgtccttc cacctcccca    3960
gccgtagctc tgcaaccacg tttcgcctgc tctgggaaaa tggcaacctc ctgcgatcgg    4020
aagagaccaa gcaaaatgag gccttctctc taacagccaa aggaaaaggc cgaggcacat    4080
tgtcggtggt ggcagtgtat catgccaaac tcaaaagcaa agtcacctgc aagaagtttg    4140
acctcagggt cagcataaga ccagcccctg agacagccaa gaagcccgag gaagccaaga    4200
ataccatgtt ccttgaaatc tgcaccaagt acttgggaga tgtggacgcc actatgtcca    4260
tcctggacat ctccatgatg actggctttg ctccagacac aaaggacctg aactgctgg    4320 cctctggagt agatagatac atctccaagt acgagatgaa caaagccttc tccaacaaga    4380
acaccctcat catctaccta gaaaagattt cacacaccga agaagactgc ctgaccttca    4440
aagttcacca gtactttaat gtgggactta tccagcccgg gtcggtcaag gtctactcct    4500
attacaacct cgaggaatca tgcacccggt tctatcatcc agagaaggac gatgggatgc    4560
tcagcaagct gtgccacagt gaaatgtgcc ggtgtgctga agagaactgc ttcatgcaac    4620
agtcacagga gaagatcaac ctgaatgtcc ggctagacaa ggcttgtgag cccggagtcg    4680
actatgtgta caagaccgag ctaaccaaca taaagctgtt ggatgatttt gatgagtaca    4740
ccatgaccat ccagcaggtc atcaagtcag gctcagatga ggtgcaggca gggcagcaac    4800
gcaagttcat cagccacatc aagtgcagaa acgccctgaa gctgcagaaa gggaagaagt    4860
acctcatgtg gggcctctcc tctgacctct ggggagaaaa gcccaacacc agctacatca    4920
ttgggaagga cacgtgggtg gagcactggc ctgaggcaga agaatgccag gatcagaagt    4980
accagaaaca gtgcgaagaa cttggggcat tcacagaatc tatggtggtt tatggttgtc    5040
ccaactgact acagcccagc cctctaataa agcttcagtt gtatttc               5087
```

<210> SEQ ID NO 4
<211> LENGTH: 1019
<212> TYPE: DNA
<213> ORGANISM: Mus musculus
<300> PUBLICATION INFORMATION:
<308> DATABASE ACCESSION NUMBER: GenBank/X66295
<309> DATABASE ENTRY DATE: 1999-03-09
<313> RELEVANT RESIDUES: (1)..(1019)

<400> SEQUENCE: 4

```
aattccggat taggcctgaa gtcccttaca ccctcaggat ggtcgttgga cccagttgcc      60
agcctcaatg tggactttgc ctgctgctgc tgtttcttct ggcccctacca ctcaggagcc    120 aggccagcgc tggctgctat gggatcccag ggatgccagg catgccgggg gcccctggga    180
```

```
aggacgggca tgatggactc caggggccca agggagagcc aggaatccca gccgtccctg      240
ggacccaagg acccaagggt cagaagggcg agcctggcat gcctggccac cgtgggaaaa      300
atggccccag gggaccctca ggttgccag gggacccagg ccccaggggg cctccggggg       360
agccaggtgt ggagggccga tacaaacaga agcaccagtc ggtattcaca gtcacccggc      420
agaccaccca gtacccagaa gccaacgccc tcgtcaggtt caactctgtg gtcaccaacc      480
ctcaggggca ttacaaccca agcacaggga agttcacctg tgaagtgccg ggcctctact      540
acttcgtcta ctacacatcg catacggcca acctgtgcgt gcacctgaac ctcaaccttg      600
ccagggtggc cagcttctgc gaccacatgt tcaacagcaa gcaggtcagc tccggaggag      660
ccctcctgcg gctccagagg ggcgacgagg tgtggctatc agtcaatgac tacaatggca      720
tggtgggcat agagggctcc aacagcgtct tctctggttt cctactgttt cccgactaga      780
acggcaggct gcttccagcc cccaaccacc cacctcgctc cctctgcttt ccccatcctc      840
actcagacct cttcctccaa gaagtccacc ctggttcctg atccatcggc cctgtgtctc      900
ctcagagttt ctctgggaac cacctaatgg tattattcct gtggccattt atcaatacct      960
tatgagacta tttttttgtt caggtggtga gatagagaaa taaatggatc accggaatt     1019

<210> SEQ ID NO 5
<211> LENGTH: 903
<212> TYPE: DNA
<213> ORGANISM: Mus musculus
<300> PUBLICATION INFORMATION:
<308> DATABASE ACCESSION NUMBER: GenBank/X82648
<309> DATABASE ENTRY DATE: 1999-03-09
<313> RELEVANT RESIDUES: (1)..(903)

<400> SEQUENCE: 5
ccccggcccg accaactgaa ggcttttaca ggctccatct cattttcctc agacttctaa       60
ggcctctcct gcagccaccc caccccaaga tggtgaccat gctgatgttc ctggccacgc      120
tggcgggtct cttcaccaca gccaaaggac aaaatttcca tcttgggaaa tgcccgtctc      180
ctcctgtgca agagaatttt gacgtgaaaa agtatcttgg aagatggtac gaaattgaga      240
agatcccagc gagctttgag aaaggaaact gcattcaagc caactactcg ctgatggaga      300
acggaaacat cgaagtgcta aacaaggagc tgagtcctga tggaaccatg aaccaagtaa      360
agggtgaagc caaacagagc aacgtctcag agccagccaa gctggaagtc cagttcttcc      420
cgttgatgcc accggcaccc tactggatcc tggccaccga ttatgaaaac tatgccctcg      480
tgtactcctg caccaccttc ttctggctct tccatgtgga ttttttttgg attcttggaa      540
gaaatcctta tctccctcca gaaacaataa cctacctaaa agatatcctt acttctaatg      600
gcatcgacat cgaaaaaatg acaacaacag atcaagcgaa ctgcccggac ttcctgtaaa      660
gggggcgggg ggggaaaacc acaccaggtt atttctttgc tttgcgttcc ctggctccac      720 cccccacgc ctcttaagta ccaagcaacc atggcaggca ctagagggag agtaaggcta      780
tagaagccaa tggagggagg ggactcatgg aaagttggcc caaacccaac ctgaccccac      840
actgtcacct tgctagccca ataataaaca ttttgctgat caaaaaaaaa aaaaaaaaa      900 aaa                                                                    903
```

METHODS OF SCREENING FOR COMPOUNDS THAT INHIBIT EXPRESSION OF BIOMARKER SEQUENCES DIFFERENTIALLY EXPRESSED WITH AGE IN MICE

CROSS-REFERENCE TO RELATED APPLICATION

This application claims priority to 60/277,382, filed Mar. 19, 2001 and incorporated by reference herein.

STATEMENT REGARDING FEDERALLY SPONSORED RESEARCH OR DEVELOPMENT

This invention was made with United States government support awarded by the following agencies: NIH CA79740. The United States has certain rights in this invention.

BACKGROUND OF THE INVENTION

A common feature of most multicellular organisms is the progressive and irreversible physiological decline that characterizes senescence. Although genetic and environmental factors can influence the aging process, the molecular basis of senescence remains unknown. Postulated mechanisms include cumulative damage to DNA leading to genomic instability, epigenetic alterations that lead to altered gene expression patterns, telomere shortening in replicative cells, oxidative damage to critical macromolecules and nonenzymatic glycation of long-lived proteins (S. M. Jazwinski, *Science* 273:54, 1996; G. M. Martin, et al., *Nature Gen.* 13:25, 1996; F. B. Johnson, et al., *Cell* 96:291, 1996; K. B. Beckman and B. N. Ames, *Physiol. Revs.* 78:547, 1998). Factors which contribute to the difficulty of elucidating mechanisms and testing interventions include the complexity of organismal senescence and the lack of molecular markers of biological age (biomarkers). Aging is complex in that underlying mechanisms in tissues with limited regenerative capacities (e.g., skeletal and cardiac muscle, brain), which are composed mainly of postmitotic (non-dividing) cells, may differ markedly from those operative in proliferative tissues. Accordingly, approaches which provide a global assessment of senescence in specific tissues would greatly increase understanding of the aging process and the possibility of pharmaceutical, genetic or nutritional intervention.

Genetic manipulation of the aging process in multicellular organisms has been achieved in *Drosophila*, through the over-expression of catalase and Cu/Zn superoxide dismutase (W. C. Orr and R. S. Sohal, *Science* 263:1128, 1994; T. L. Parkes, et al., *Nat. Genet.* 19:171, 1998), in the nematode *C. elegans*, through alterations in the insulin receptor signaling pathway (S. Ogg, et al., *Nature* 389:994, 1997; S. Paradis and G. Ruvkun, *Genes Dev.* 12:2488–2498, 1998; H. A. Tissenbaum and G. Ruvkun, *Genetics* 148:703, 1998), and through the selection of stress-resistant mutants in either organism (T. E. Johnson, *Science* 249:908, 1990; S. Murakami and T. E. Johnson, *Genetics* 143:1207, 1996; Y. J. Lin, et al., *Science* 282:943, 1998). In mammals, there has been limited success in the identification of genes that control aging rates. Mutations in the Werner Syndrome locus (WRN) accelerate the onset of a subset of aging-related pathology in humans, but the role of the WRN gene product in the modulation of normal aging is unknown (C. E. Yu, et al., *Science* 272:258, 1996; D. B. Lombard and L. Guanrente, *Trends Genet.* 12:283, 1996).

In contrast to the current lack of genetic interventions to retard the aging process in mammals, caloric restriction (CR) appears to slow the intrinsic rate of aging (R. Weindruch and R. L. Walford, *The Retardation of Aging and Disease by Dietary Restriction* (C C. Thomas, Springfield, Ill., 1988; L. Fishbein, Ed., *Biological Effects of Dietary Restriction* (Springer-Verlag, New York, 1991; B. P. Yu, Ed., *Modulation of Aging Processes by Dietary Restriction* (CRC Press, Boca Raton, Fla. 1994). Most studies have involved laboratory rodents which, when subjected to a long-term, 25–50% reduction in calorie intake without essential nutrient deficiency, display delayed onset of age-associated pathological and physiological changes and extension of maximum lifespan.

BRIEF DESCRIPTION OF THE SEVERAL VIEWS OF THE DRAWINGS

FIGS. 1–23 are individual bar graphs disclosing the fold change of messages and lines showing signal intensities corresponding to individual sequences in young and old tissue.

FIG. 1 discloses changes in M21050.
FIG. 2 discloses changes in Z49204.
FIG. 3 discloses changes in U49430.
FIG. 4 discloses changes in K02782.
FIG. 5 discloses changes in X58861.
FIG. 6 discloses changes in X66295.
FIG. 7 discloses changes in M22531.
FIG. 8 discloses changes in X67809.
FIG. 9 discloses changes in U19118.
FIG. 10 discloses changes in M64086.
FIG. 11 discloses changes in M63695.
FIG. 12 discloses changes in U39066.
FIG. 13 discloses changes in X92590.
FIG. 14 discloses changes in X56518.
FIG. 15 discloses changes in AA182189.
FIG. 16 discloses changes in X16493.
FIG. 17 discloses changes in X60452.
FIG. 18 discloses changes in U20344.
FIG. 19 discloses changes in X16834.
FIG. 20 discloses changes in X82648.
FIG. 21 discloses changes in D00754.
FIG. 22 discloses changes in D16313.
FIG. 23 discloses changes in 15789.

DESCRIPTION OF THE INVENTION

Figure 1:
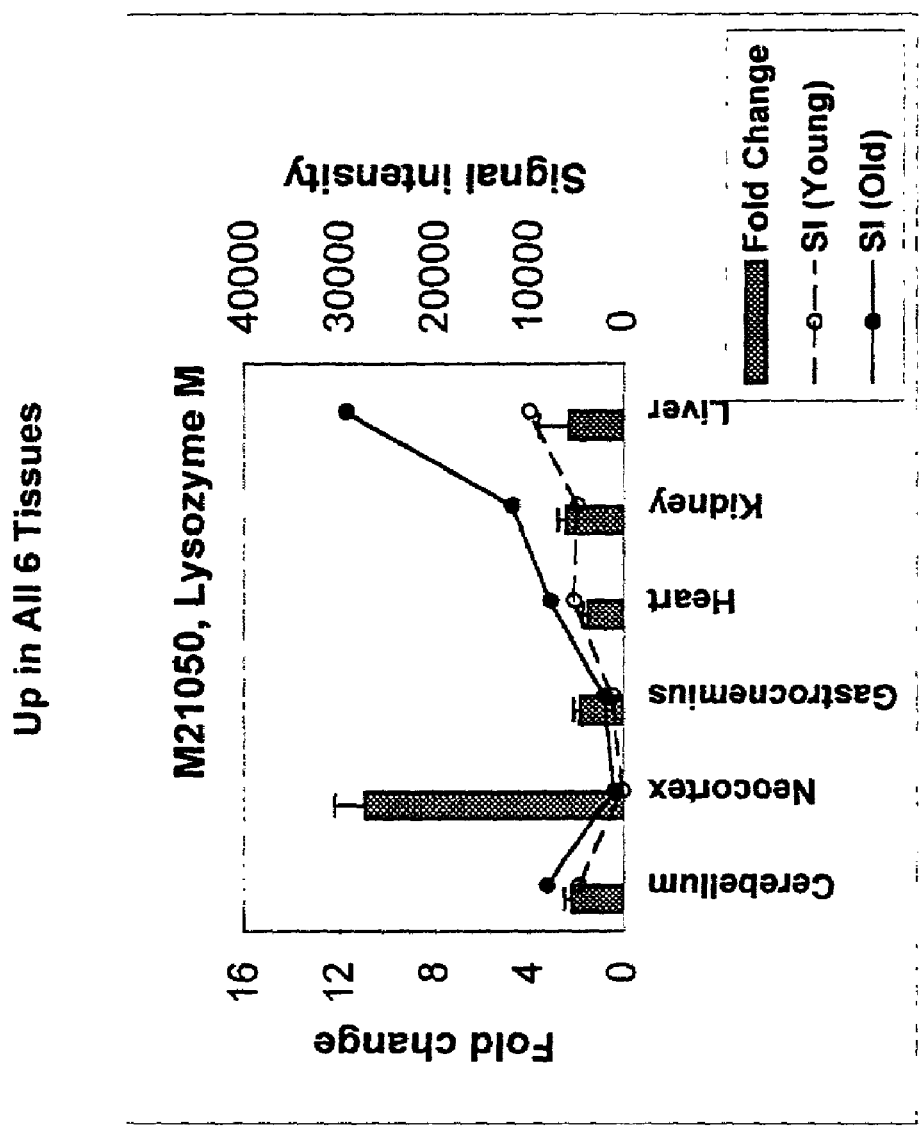
Figure 2:
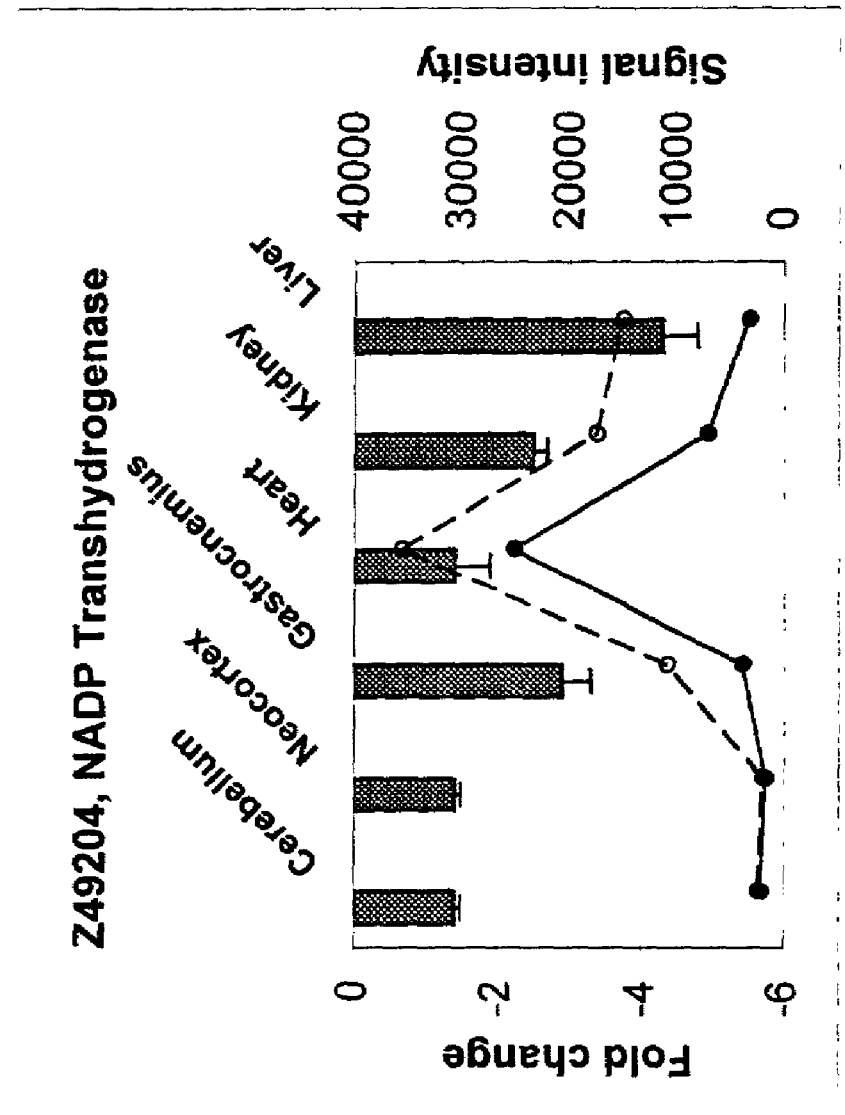
Figure 8:
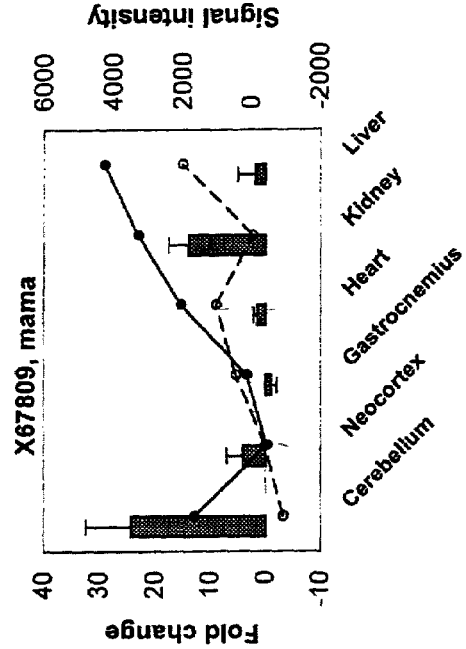
Figure 9:
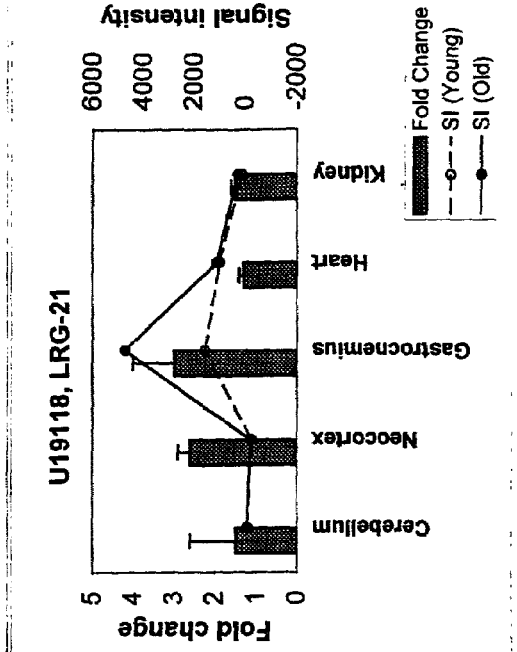
Figure 7:
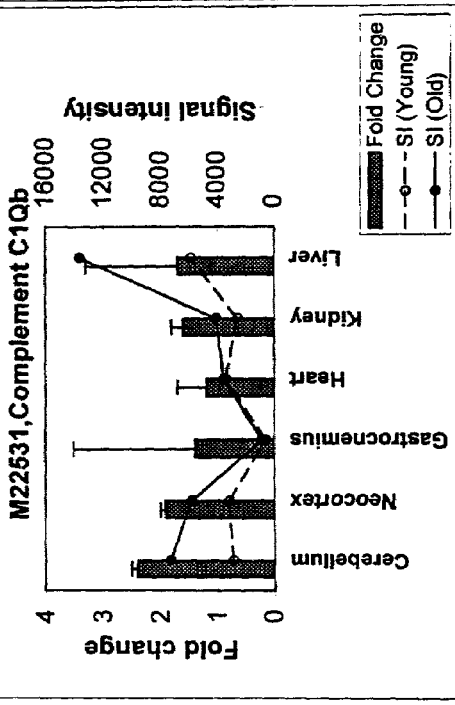
Figure 10:
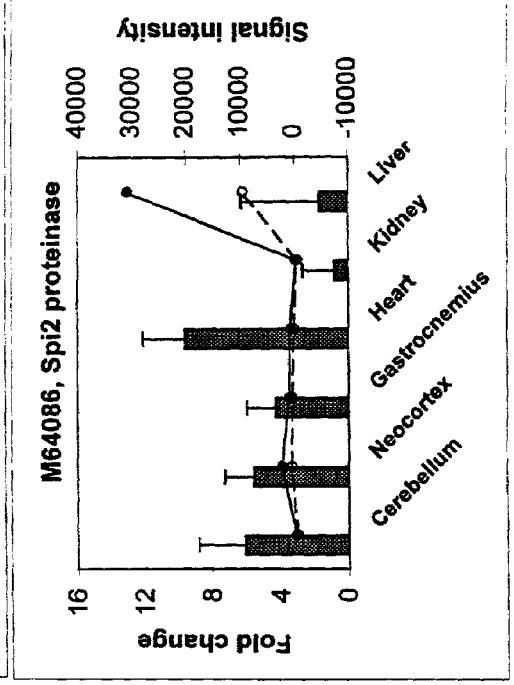
Figure 15:
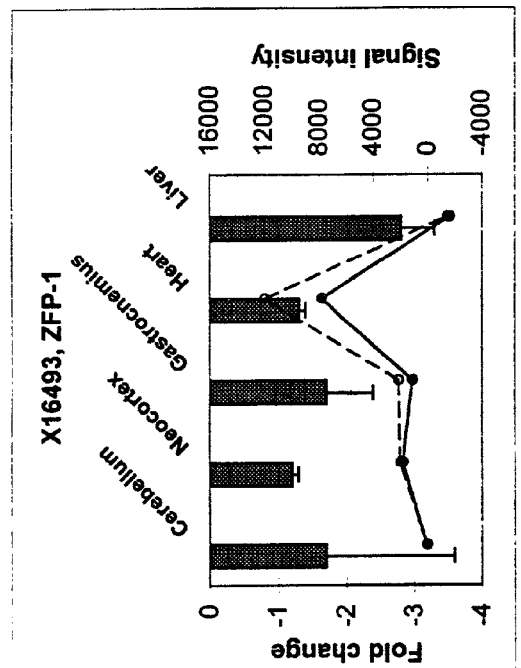
Figure 16:
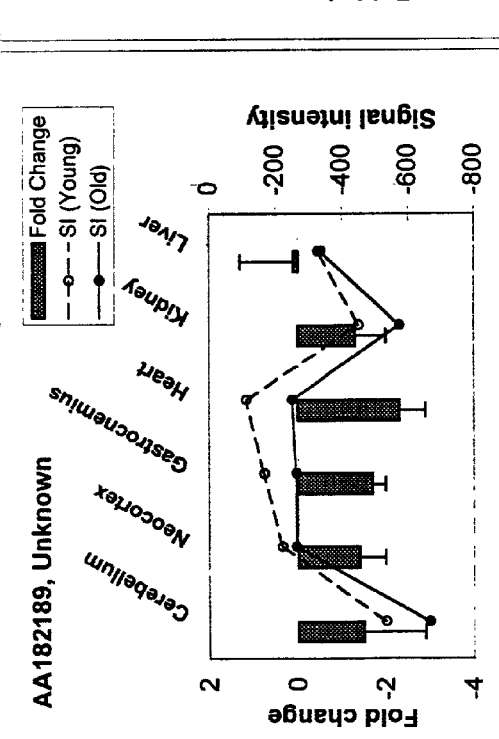
Figure 17:
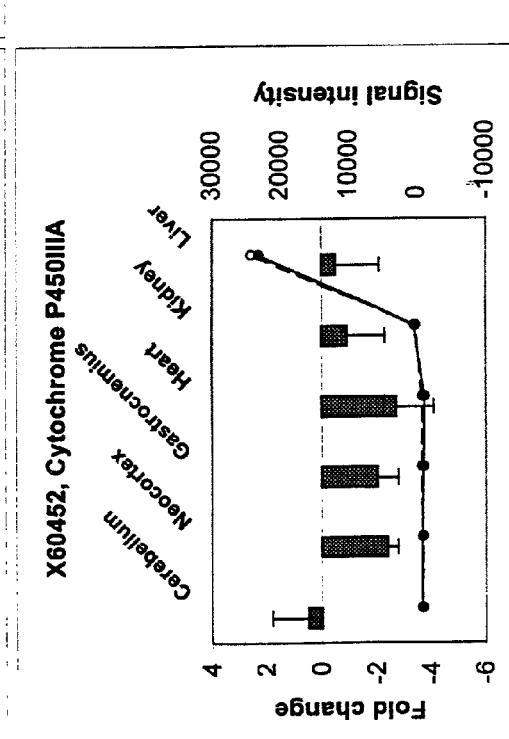
Figure 18:
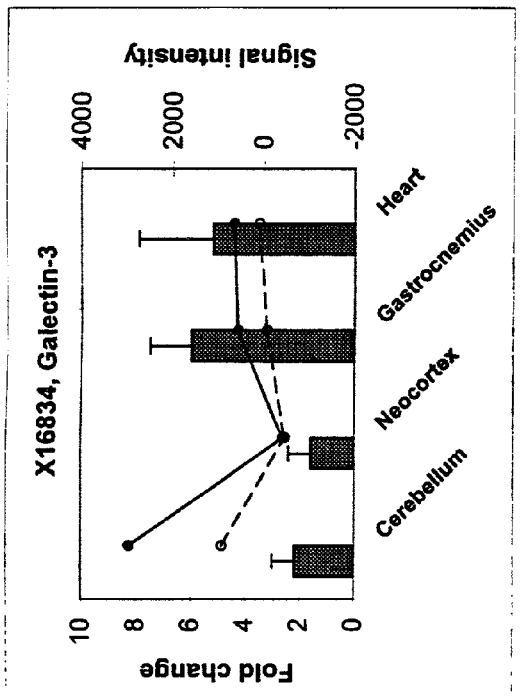
Figure 19:
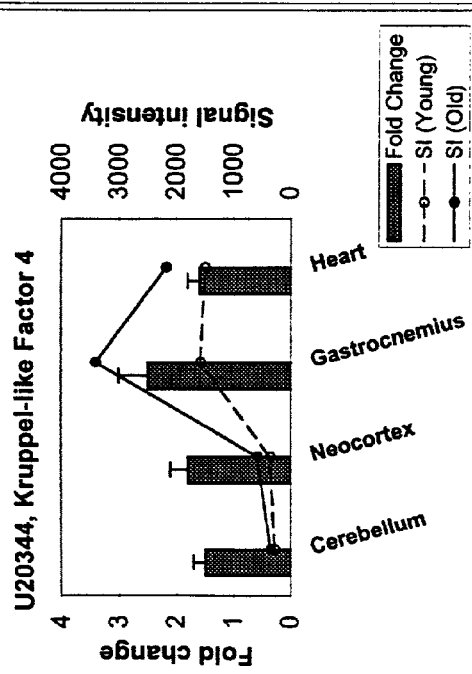
Figure 20:
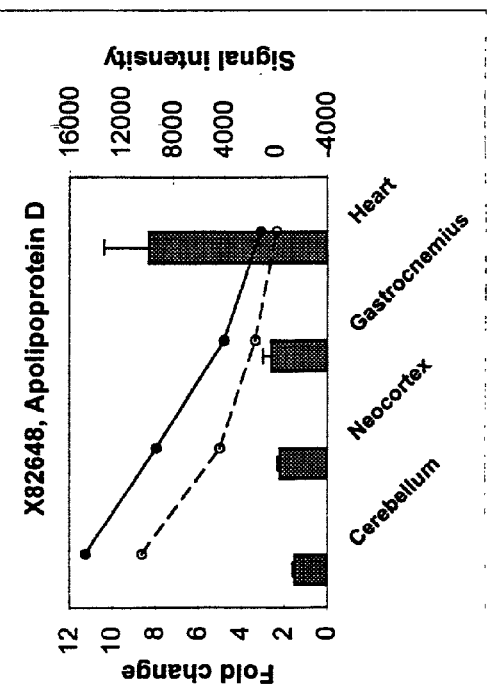

In order to generate rational interventions to retard aging and associated diseases, identification of molecular targets is required. To achieve this goal, we used the new U74 and 11K Affymetrix (Santa Clara, Calif.) murine genome DNA chips to measure the gene expression profile associated with the aging process for 11,000 genes in six tissues from mice: cerebral cortex, cerebellum, skeletal muscle (gastrocnemius), heart, liver and kidney. Six animals were used per experiment (3 young and 3 old), resulting in a total of 396,000 independent gene expression measurements. To our knowledge, this study represents the largest search ever performed for gene expression alterations as a function of age.

We reasoned that alterations in gene expression that are shared among 5 to 6 tissues, or among the four post-mitotic tissues studied (i.e., cerebellum, neocortex, gastrocnemius and heart) must represent fundamental changes associated with aging as opposed to tissue-specific effects that are secondary to the aging process.

An additional requirement for the evaluation of therapies that retard the aging process is the development of aging biomarkers. A suitable biomarker of the aging process should reflect biological age (physiological condition) as opposed to chronological age. Additionally, the biomarker should be amenable to quantitation and reflect aging-related alterations at the molecular level in the tissue under study.

By "biological age" we mean the physiological state of an animal or tissue relative to the physiological changes that occur throughout the animal's lifespan. By "chronological age" we mean the age of an animal as measured by a time scale, such as month or years.

There exists a large and growing segment of the population in developed countries that is suffering from age-associated disorders, such as sarcopenia (loss of muscle mass), neurodegenerative conditions, and cardiac disease. Therefore, the market for compounds that prevent aging-associated disorders and improve quality of life for the elderly is likely to drive research and development of novel drugs by the pharmaceutical industry. As an example, many drugs, nutraceuticals and vitamins are thought to influence aging favorably, but their use remains limited due to the lack of FDA approval. The inability to assess biological aging in tissues at the molecular level precludes proper animal and human testing of such compounds.

In one embodiment, the invention is a method for measuring the relative biological aging process of a multicellular organism, such as a mammal, at the organ, tissue or cellular level through the characterization of the organism's gene expression patterns. This method preferably comprises obtaining a cDNA copy of the organism's RNA and determining the expression pattern of at least one of the genes listed in Table 2 (genes which change in expression with aging in multiple tissues), preferably at least 5 biomarker sequences, most preferably at least 10 biomarker sequences and more preferably at least 20, 30, 40, or 50 biomarker sequences, within the cDNA. By "gene expression pattern" we mean to include the change in pattern of the encoded RNA or protein.

One may characterize the biological age of the organism by determining how many and at what level these genes disclosed are altered in expression. Because the genes listed in Table 2 are age-related alterations in multiple tissues, one could use the same genes to determine biological aging in multiple tissues, such as, but not limited to, neocortex, heart, cerebellum, kidney, liver and skeletal muscle.

In some embodiments, gene expression is measured by identifying the presence or amount of one or more proteins encoded by one of the genes listed in Table 2.

The present invention also provides systems for detecting two or more markers of interest (e.g., two or more markers from Table 2). For example, where it is determined that a finite set of particular markers provides relevant information, a detection system is provided that detects the finite set of markers. For example, as opposed to detecting all genes expressed in a tissue with a generic microarray, a defined microarray or other detection technology is employed to detect the plurality (e.g., 2, 5, 10, 25) of markers that define a biological condition (e.g., a biological age, a response to a pharmaceutical or diet that increases or decreases rate of aging, etc.).

The present invention is not limited by the method in which biomarkers are detected or measured. In some embodiments, mRNA, cDNA, or protein is detected in tissue samples (e.g., biopsy samples). In other embodiments, mRNA, cDNA, or protein is detected in bodily fluids (e.g., serum, plasma, urine, or saliva). The present invention further provides kits for the detection of biomarkers.

In some preferred embodiments, protein is detected. Protein expression may be detected by any suitable method. In some embodiments, proteins are detected by binding of an antibody specific for the protein. For example, in some embodiments, antibody binding is detected using a suitable technique, including but not limited to, radioimmunoassay, ELISA (enzyme-linked immunosorbant assay), "sandwich" immunoassays, immunoradiometric assays, gel diffusion precipitation reactions, immunodiffusion assays, in situ immunoassays (e.g., using colloidal gold, enzyme or radio-isotope labels, for example), Western blots, precipitation reactions, agglutination assays (e.g., gel agglutination assays, hemagglutination assays, etc.), complement fixation assays, immunofluorescence assays, protein A assays, immunoelectrophoresis assays, and proteomic assays, such as the use of gel electrophoresis coupled to mass spectroscopy to identify multiple proteins in a sample.

In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many methods are known in the art for detecting binding in an immunoassay and are within the scope of the present invention.

In some embodiments, an automated detection assay is utilized. Methods for the automation of immunoassays include, but are not limited to, those described in U.S. Pat. Nos. 5,885,530; 4,981,785; 6,159,750; and 5,358,691, each of which is herein incorporated by reference. In some embodiments, the analysis and presentation of results is also automated. For example, in some embodiments, software that generates a diagnosis and/or prognosis based on the presence or absence of a series of proteins corresponding to markers is utilized.

In other embodiments, the immunoassay described in U.S. Pat. Nos. 5,599,677 and 5,672,480, each of which is herein incorporated by reference, is utilized. In other embodiments, proteins are detected by immunohistochemistry.

In other embodiments, markers are detected at the level of CDNA or RNA. In some embodiments of the present invention, markers are detected using a direct sequencing technique. In these assays, nucleic acid samples are first isolated from a subject using any suitable method. In some embodiments, the region of interest is cloned into a suitable vector and amplified by growth in a host cell (e.g., bacteria). In other embodiments, DNA in the region of interest is amplified using PCR. Following amplification, DNA in the region of interest is sequenced using any suitable method, including but not limited to manual sequencing using radioactive marker nucleotides, or automated sequencing. The results of the sequencing are displayed using any suitable method.

In some embodiments of the present invention, markers are detected using a PCR-based assay. In yet other embodiments, reverse-transcriptase PCR (RT-PCR) is used to detect the expression of RNA. In RT-PCR, RNA is enzymatically converted to complementary DNA or "cDNA" using a reverse transcriptase enzyme. The cDNA is then used as a template for a PCR reaction. PCR products can be detected by any suitable method, including but not limited to, gel electrophoresis and staining with a DNA specific stain or hybridization to a labeled probe. In some embodiments, the quantitative reverse transcriptase PCR with standardized mixtures of competitive templates method described in U.S. Pat. Nos. 5,639,606, 5,643,765, and 5,876,978 (each of which is herein incorporated by reference) is utilized.

In preferred embodiments of the present invention, markers are detected using a hybridization assay. In a hybridization assay, the presence of absence of a marker is determined based on the ability of the nucleic acid from the sample to hybridize to a complementary nucleic acid molecule (e.g., an oligonucleotide probe). A variety of hybridization assays using a variety of technologies for hybridization and detection are available.

In some embodiments, hybridization of a probe to the sequence of interest is detected directly by visualizing a bound probe (e.g., a Northern or Southern assay; See e.g., Ausabel, et al. (eds.), *Current Protocols in Molecular Biology*, John Wiley & Sons, NY [1991]). In these assays, DNA (Southern) or RNA (Northern) is isolated. The DNA or RNA is then cleaved with a series of restriction enzymes that cleave infrequently in the genome and not near any of the markers being assayed. The DNA or RNA is then separated (e.g., on an agarose gel) and transferred to a membrane. A labeled (e.g., by incorporating a radionucleotide) probe or probes is allowed to contact the membrane under low, medium, or high stringency conditions. Unbound probe is removed and the presence of binding is detected by visualizing the labeled probe.

In some embodiments, the DNA chip assay is a GeneChip (Affymetrix, Santa Clara, Calif.; See e.g., U.S. Pat. Nos. 6,045,996; 5,925,525; and 5,858,659; each of which is herein incorporated by reference) assay. The GeneChip technology uses miniaturized, high-density arrays of oligonucleotide probes affixed to a "chip." Probe arrays are manufactured by Affymetrix's light-directed chemical synthesis process, which combines solid-phase chemical synthesis with photolithographic fabrication techniques employed in the semiconductor industry. Using a series of photolithographic masks to define chip exposure sites, followed by specific chemical synthesis steps, the process constructs high-density arrays of oligonucleotides, with each probe in a predefined position in the array. Multiple probe arrays are synthesized simultaneously on a large glass wafer. The wafers are then diced, and individual probe arrays are packaged in injection-molded plastic cartridges, which protect them from the environment and serve as chambers for hybridization.

The nucleic acid to be analyzed is isolated, amplified by PCR, and labeled with a fluorescent reporter group. The labeled DNA is then incubated with the array using a fluidics station. The array is then inserted into the scanner, where patterns of hybridization are detected. The hybridization data are collected as light emitted from the fluorescent reporter groups already incorporated into the target, which is bound to the probe array. Probes that perfectly match the target generally produce stronger signals than those that have mismatches. Since the sequence and position of each probe on the array are known, by complementarity, the identity of the target nucleic acid applied to the probe array can be determined.

In other embodiments, a DNA microchip containing electronically captured probes (Nanogen, San Diego, Calif.) is utilized (See e.g., U.S. Pat. Nos. 6,017,696; 6,068,818; and 6,051,380; each of which are herein incorporated by reference). Through the use of microelectronics, Nanogen's technology enables the active movement and concentration of charged molecules to and from designated test sites on its semiconductor microchip. DNA capture probes unique to a given marker are electronically placed at, or "addressed" to, specific sites on the microchip. Since nucleic acid molecules have a strong negative charge, they can be electronically moved to an area of positive charge.

In still further embodiments, an array technology based upon the segregation of fluids on a flat surface (chip) by differences in surface tension (ProtoGene, Palo Alto, Calif.) is utilized (See e.g., U.S. Pat. Nos. 6,001,311; 5,985,551; and 5,474,796; each of which is herein incorporated by reference). Protogene's technology is based on the fact that fluids can be segregated on a flat surface by differences in surface tension that have been imparted by chemical coatings. Once so segregated, oligonucleotide probes are synthesized directly on the chip by ink-jet printing of reagents.

In yet other embodiments, a "bead array" is used for the detection of markers (Illumina, San Diego, Calif.; See e.g., PCT Publications WO 99/67641 and WO 00/39587, each of which is herein incorporated by reference). Illumina uses a BEAD ARRAY technology that combines fiber optic bundles and beads that self-assemble into an array. Each fiber optic bundle contains thousands to millions of individual fibers depending on the diameter of the bundle. The beads are coated with an oligonucleotide specific for the detection of a given marker. Batches of beads are combined to form a pool specific to the array. To perform an assay, the BEAD ARRAY is contacted with a prepared sample. Hybridization is detected using any suitable method.

In some embodiments of the present invention, hybridization is detected by enzymatic cleavage of specific structures (e.g., INVADER assay, Third Wave Technologies; See e.g., U.S. Pat. Nos. 5,846,717, 6,090,543; 6,001,567; 5,985,557; and 5,994,069; each of which is herein incorporated by reference). In some embodiments, hybridization of a bound probe is detected using a TaqMan assay (PE Biosystems, Foster City, Calif.; See e.g., U.S. Pat. Nos. 5,962,233 and 5,538,848, each of which is herein incorporated by reference). The assay is performed during a PCR reaction. The TaqMan assay exploits the 5'-3' exonuclease activity of DNA polymerases such as AMPLITAQ DNA polymerase. A probe, specific for a given marker, is included in the PCR reaction. The probe consists of an oligonucleotide with a 5'-reporter dye (e.g., a fluorescent dye) and a 3'-quencher dye. During PCR, if the probe is bound to its target, the 5'-3' nucleolytic activity of the AMPLITAQ polymerase cleaves the probe between the reporter and the quencher dye. The separation of the reporter dye from the quencher dye results in an increase of fluorescence. The signal accumulates with each cycle of PCR and can be monitored with a fluorimeter.

Additional detection assays that are produced and utilized using the systems and methods of the present invention include, but are not limited to, enzyme mismatch cleavage methods (e.g., Variagenics, U.S. Pat. Nos. 6,110,684; 5,958,692; 5,851,770, herein incorporated by reference in their entireties); branched hybridization methods (e.g., Chiron, U.S. Pat. Nos. 5,849,481; 5,710,264; 5,124,246; and 5,624,802, herein incorporated by reference in their entireties); rolling circle replication (e.g., U.S. Pat. Nos. 6,210,884 and 6,183,960, herein incorporated by reference in their entireties); NASBA (e.g., U.S. Pat. No. 5,409,818, herein incorporated by reference in its entirety); molecular beacon technology (e.g., U.S. Pat. No. 6,150,097, herein incorporated by reference in its entirety); E-sensor technology (Motorola, U.S. Pat. Nos. 6,248,229; 6,221,583; 6,013,170;

and 6,063,573, herein incorporated by reference in their entireties); cycling probe technology (e.g., U.S. Pat. Nos. 5,403,711; 5,011,769; and 5,660,988, herein incorporated by reference in their entireties); ligase chain reaction (Barnay, *Proc. Natl. Acad. Sci. USA* 88:189–93, 1991); and sandwich hybridization methods (e.g., U.S. Pat. No. 5,288,609, herein incorporated by reference in its entirety).

In some embodiments, mass spectroscopy is used to detect markers. For example, in some embodiments, a MassARRAY system (Sequenom, San Diego, Calif.) is used to detect markers (See e.g., U.S. Pat. Nos. 6,043,031; 5,777,324; and 5,605,798; each of which is herein incorporated by reference).

In some embodiments, the present invention provides kits for the identification, characterization, and quantitation of markers. In some embodiments, the kits contain antibodies specific for markers, in addition to detection reagents and buffers. In other embodiments, the kits contain reagents specific for the detection of nucleic acid (e.g., oligonucleotide probes or primers). In preferred embodiments, the kits contain all of the components necessary to perform a detection assay, including all controls, directions for performing assays, and any necessary software for analysis and presentation of results. In some embodiments, the kits contain instructions including a statement of intended use as required by the Environmental Protection Agency or U.S. Food and Drug Administration for the labeling of in vitro diagnostic assays and/or of pharmaceutical or food products.

Comparison of the organism's gene expression pattern with the result expressed in Table 2 would indicate whether the organism has an aberrant gene expression profile which may indicate that the organism is either biologically younger or older than the chronological age would indicate.

In another embodiment, the present invention is a method of screening a test compound for the ability to inhibit, retard or reverse the aging process in mammalian tissue. In a typical example of this embodiment, one would first treat a test mammal with a test compound and then analyze a representative tissue of the mammal for the level of expression of the genes which change in expression in multiple tissues (Table 2). Preferably, the tissue is selected from the group consisting of brain tissue, heart tissue, muscle tissue, skeletal muscle, kidney, heart and liver tissue. One then compares the analysis of the tissue with a control, untreated mammal and identifies test compounds that are capable of modifying the expression of the biomarker sequences in the mammalian samples such that the expression is indicative of tissue that has an inhibited or retarded biological age. This expression pattern would be more similar to an expression pattern found in biologically younger subjects.

As an example, a group of young rodents (e.g., mice) would be divided into a control and a test group. The test group would receive a test compound such as a dietary supplement added to food from age 5 months to 30 months, whereas the control group would receive a standard diet during this time period. At age 30 months, several tissues would be collected from animals from each group and a gene expression profile of at least one of the genes listed in Table 2 (preferably at least five genes) would be obtained and would be compared to the profile of young animals (5 month old). One would then determine whether, for any of the organs investigated, the gene expression pattern of the animals receiving the test compound was more similar to that of young animals, indicating that aging has been retarded.

In another embodiment of the present invention, one would use the sequences of the genes disclosed in Table 2 for a therapy for anti-aging or preventing, retarding or reversing age-associated disorders. In general, one would try to amplify gene expression for the genes identified herein as decreasing during the aging process and decrease the expression of genes identified herein as increased during the aging process. For example, one might try to decrease the expression of lysozyme M (M21050), which is shown herein to be induced by at least 1.5-fold in all examined tissues. One would attempt to increase the expression of NADP transhydrogenase (Z49204), which has been shown herein to decrease in expression in the tissues. Common methods of increasing and decreasing expression would be known to one of skill in the art. Examples for supplementation of expression would include supplying the organism with additional copies of the gene. A preferred example for decreasing expression would include RNA antisense technologies or pharmaceutical intervention.

The genes disclosed in Table 2 would be appropriate drug development targets. One would use the information presented in the present application for drug development by using currently existing, or by developing, pharmaceutical compounds that either mimic or inhibit the activity of the genes listed in Table 2, or the proteins encoded by these genes.

Therefore, the biomarker genes disclosed herein represent targets for pharmaceutical development and gene therapy or RNA antisense therapy with the goal of preventing, retarding or reversing the aging process at the molecular level. These gene expression alterations may also play a role in age-related diseases of the organs under study. Additionally, these genes represent biomarkers of the aging process that can be used for diagnostic purposes.

In a particularly preferred form of the present invention, the targeted genes or proteins would be encoded by ORFs M21050 (SEQ ID NO: 1), Z49204, U49430 (SEQ ID NO: 2), K02782 (SEQ ID NO: 3), X58861, X66295 (SEQ ID NO: 4), M22531, M64086, U39066, X56518, X16834, X82648 (SEQ ID NO: 5) and L38971.

The present invention further provides methods for selecting subjects (e.g., humans and animals) that are appropriate targets for a particular therapy. In some such embodiments, a sample from the subject is tested for one or more markers (e.g., markers in Table 2). The expression profile of the subject is then used to select a therapy appropriate for that individual's specific condition.

The present invention also provides expression profiles. In some such embodiments, a test sample is assayed for the presence of one or more biomarkers and compared to the expression profile, for example, to determine the biological age of the sample and/or to determine the effect of a diet or other therapy on the sample. The present invention is not limited by the form of the expression profile. In some embodiments, the expression profile is maintained in computer software. In some embodiments, the expression profile is written material. The present invention is not limited by the number of markers provided or displayed in an expression profile. For example, the expression profile may comprise two or more markers found in Table 2, indicating a biological status of a sample.

The present invention further provides databases comprising expression information (e.g., expression profiles comprising one or more markers from Table 2 from one or more samples). In some embodiments, the databases find use in data analysis, including, but not limited to, comparison of markers to one or more public or private information databases (e.g., OMIM, GenBank, BLAST, Molecular Modeling Databases, Medline, genome databases, etc.). In some such embodiments, an automated process is carried out to automatically associate information obtained from data obtained using the methods of the present invention to information in one or more of public or private databases. Associations find use, for example, in making expression correlations to phenotypes (e.g., disease states).

The present invention also provides methods for selecting ingredients in food or dietary products (e.g., nutraceuticals) and food and dietary products thus generated. For example, a food or dietary product is altered (e.g., supplemented or depleted) with a factor that increases or decreases, directly or indirectly, the expression of one or more age-related markers (e.g., markers in Table 2). In some embodiments, the food or dietary product is altered with a factor that might increase or decrease, directly or indirectly, the expression of one or more age-related markers (e.g., markers in Table 2).

For example, it has been shown that apolipoprotein D expression is induced by retinoic acid (e.g., Lopez-Boado, et al., *J. Biol. Chem.* 271:32105, 1996). As shown in Table 2, apolipoprotein D expression is altered in an age-related manner. Thus, in some embodiments of the present invention, food or dietary products are altered to increase or decrease retinoic acid concentrations (or compounds with similar biologic activity), directly or indirectly, and are prescribed, marketed, and/or labeled as having an effect on biological age. In some preferred embodiments of the present invention the food or dietary product is altered to affect a plurality of markers (e.g., two or more markers in Table 2).

We also understand the present invention to be extended to mammalian homologs of the mouse genes listed in Table 2. One of skill in the art could easily investigate homologs in other mammalian species by identifying particular genes with sufficiently high homology to the genes listed in Table 2. By "high homology" we mean that the homology is at least 50% overall (within the entire gene or protein) either at the nucleotide or amino acid level.

EXAMPLES

Methods

A. Animal Ages, Husbandry and Dietary Manipulations.

All aspects of animal care were approved by the appropriate committees and conformed with institutional guidelines. Details on the methods employed to house and feed male C57 BL6 ("B6") mice, a commonly used model in aging research with an average lifespan of ~30 months, were recently described (Pugh, et al., 1999). Briefly, mice were purchased from Charles River Laboratories (Wilmington, Mass.) at 1.5 months of age. After receipt in Madison, the mice were housed singly in the specific pathogen-free Shared Aging Rodent Facility at the Madison Va. Geriatric Research, Education and Clinical Center, and provided a nonpurified diet (PLI 5001 [Purina Labs, St. Louis, Mo.]) and acidified water ad libitum for one week. Each mouse in the control group was fed 84 kcal/week of the diet (TD91349 [Teklad, Madison, Wis.]).

B. Gene Expression Analysis.

All experiments use three mice per experimental group (i.e., young and old). RNA from each animal is independently hybridized to DNA chips, so that intragroup variability is known. Our own data indicate that variability between animals in the same age/diet group is minimal, since we have never observed correlation coefficients between two animals to be <0.98. Mice were euthanized by rapid cervical dislocation and autopsied to exclude animals showing overt disease. The brain was dissected and sectioned along the midline. One-half of the brain was used for microarray analysis. The samples were placed in a microcentrifuge tube, immediately flash-frozen in liquid nitrogen, and stored at −80° C.

Total RNA was extracted from frozen tissues using TRIZOL reagent (Life Technologies) and a power homogenizer (Fisher Scientific) with the addition of chloroform for the phase separation before isopropyl alcohol precipitation of total RNA. Poly $(A)^+$ RNA is purified from the total RNA with oligo-dT linked Oligotex resin (Qiagen). Two micrograms of poly $(A)^+$ RNA are converted into double-stranded cDNA (ds-cDNA) using SuperScript Choice System (Life Technologies) with an oligo dT primer containing a T7 RNA polymerase promoter region (Genset). After second strand synthesis, the reaction mixture is extracted with phenol/chloroform/isoamyl alcohol. Phase Lock Gel (5 Prime→3 Prime, Inc.) is used to increase ds-cDNA recovery. The ds-cDNA is collected by ethanol precipitation. The pellet is resuspended in 3 μl of DEPC-treated water. In vitro transcription is performed using a T7 Megascript Kit (Ambion) with 1.5 μl of ds-cDNA template in the presence of a mixture of unlabeled ATP, CTP, GTP, and UTP and biotin-labeled CTP and UTP (bio-11-CTP and bio-16-UTP [Enzo]). Biotin-labeled cRNA is purified using a Rneasy affinity column (Qiagen). The amount of biotin-labeled cRNA is determined by measuring absorbency at 260 nm. Biotin-labeled cRNA is fragmented randomly to sizes ranging from 35 to 200 bases by incubating at 94° C. for 35 minutes in 40 mM Trisacetate pH 8.1, 100 mM potassium acetate, and 30 mM magnesium acetate. The hybridization solutions contain 100 mM MES, 1 M [Na$^+$], 20 mM EDTA, and 0.01% Tween 20. The hybridization solutions also contained 50 pM oligonucleotide B2 (a biotin-labeled control oligonucleotide used for making grid alignments), 0.1 mg/mL herring sperm DNA, and 0.5 mg/mL acetylated BSA. The final concentration of fragmented cRNA is 0.05 μg/pl in the hybridization solutions. Hybridization solutions are heated to 99° C. for 5 minutes followed by 45° C. for 5 minutes before being placed in the gene chip. 10 μg of cRNA is placed in the gene chip. Hybridizations were carried out at 45° C. for 16 hours with mixing on a rotisserie at 60 rpm. Following hybridization, the hybridization solutions are removed, and the gene chips installed in a fluidics system for wash and stain. The fluidics system (Affymetrix GeneChip Fluidics Station 400) performs two post hybridization washes (a non-stringent wash and a stringent wash), staining with streptavidin-phycoerythrin, and one post-stain wash. The gene chips were read at a resolution of 6 μm using a Hewlett Packard GeneArray Scanner. Data collected from two scanned images are used for the analysis.

C. Data Analysis Performed by Affymetrix Software.

Detailed protocols for data analysis of Affymetrix microarrays and extensive documentation of the sensitivity and quantitative aspects of the method have been described (Lockheart, et al., 1996). The U74 and the 11K series are derived from UniGene, which is available on the World Wide Web at the National Center for Biotechnology Information web page. Briefly, each gene is represented by the use of ~20 perfectly matched (PM) and an equal number of mismatched (MM) control probes. The MM probes act as specificity controls that allow the direct subtraction of both background and cross-hybridization signals. The number of instances in which the PM hybridization signal is larger than the MM signal is computed along with the average of the logarithm of the PM:MM ratio (after background subtraction) for each probe set. These values are used to make an arbitrary matrix-based decision concerning the presence or absence of an RNA molecule which serves as an indicator of data quality. All calculations are performed by Affymetrix software. To determine the quantitative RNA abundance, the average of the differences representing PM minus MM for each gene-specific probe family is calculated, after discarding the maximum, the minimum, and any outliers beyond three standard deviations. This value, termed the Average Intensity Difference (SI), is a function of mRNA abundance. In order to make comparisons between data-sets, the Average Intensity Differences for each gene are normalized to the total fluorescence intensity of the array. This is similar to the concept of normalizing signal to a reference mRNA, such as β-actin in a typical Northern blot.

In order to calculate fold changes (FC) between data sets (after normalization) obtained from young (y) vs. old (o) mice, the following formula is used by the software:

$$FC = \frac{SI_o - SI_y}{\text{the smallest of either } SI_y \text{ or } SI_o} + 1 \text{ if } SI_o \geq SI_o \text{ or } -1 \text{ if } SI_o < SI_y$$

Where $SI_o$ is the average signal intensity from a gene-specific probe family from an old mouse and $SI_y$ is that from a young mouse. Alternatively, if the $Q_{factor}$, a measure of the non-specific fluorescence intensity background, is larger the smallest of either $SI_y$ or $SI_o$, the FC is calculated as:

$$FC = \frac{SI_o - SI_y}{Q_{factor}}$$

The $Q_{factor}$ is automatically calculated for different regions of the microarray and, therefore, minimizes the calculation of spurious fold changes. Average of pairwise comparisons are made between study groups, each composed of three animals, using Excel software. For example, each tissue from 5-month-old mice (n=5) is compared to 30-month-old mice (n=3), generating a total of 9 pairwise comparisons. No correlation coefficient between two animals in the same age/diet group was less than 0.98, suggesting that variations between individuals are small within the same age/diet group.

D. Numbers of Genes Selected as Biomarkers.

The numbers of genes identified showing shared changes in expression with aging in 5–6 of the tissues examined are summarized in Table 1. We have also included the genes that showed either up-regulation or down-regulation in all four tissues studied that are composed mainly of post-mitotic cells (non-dividing), gastrocnemius, heart, cerebellum and neocortex. The procedure involved a computer search of our database to identify those genes which showed 1.3-fold or greater increases or decreases in expression with aging in either five or all six of the tissues examined. The data supporting the change was then critically evaluated for data quality based on information provided by Affymetrix software as well as signal intensity (which also provides information on tissue-specific expression levels), and variation (standard error).

TABLE 1

Overview of Numbers of Genes Displaying
Shared Changes in Expression with Aging in Multiple Tissues

| | Number of Tissues Showing Aging Change | | | | Four (G, H, N, C only) | |
|---|---|---|---|---|---|---|
| Direction of Age | Six | | Five | | | |
| Change | All | Selected* | All | Selected | All | Selected |
| Increase | 1 | 1 | 9 | 8 | 3 | 3 |
| Decrease | 2 | 1 | 12 | 6 | 11 | 4 |

*Only genes that displayed SEM + 1.3 < observed fold change in at least 3 tissues were selected for inclusion in this table.

Synopsis of Shared Changes in Gene Expression with Aging.

A. Genes Altered in Expression in All Six Tissues.

Only one gene, Lysozme M (ORF M21050), was induced by 1.5-fold (50%) or higher in all tissues, whereas only one gene, NADP transhydrogenase, was decreased in expression by 50% or more in all tissues studied.

Lysozyme M is a proinflammatory mediator associated with the monocyte-macrophage system (Cross, et al., 1988). Lysozymes have primarily bacteriolytic function; those in tissues and body fluids are associated with the monocyte-macrophage system and enhance the activity of immunoagents. The enzyme catalyzes the hydrolysis of the 1,4-beta-linkages between N-acetyl-d-glucosamine and n-acetylmuramic acid in peptidoglycan heteropolymers of prokaryotic cell walls.

NADP transhydrogenase (Z49204) catalyzes transhydrogenation between NADH and NADP and is coupled to respiration and ATP hydrolysis. The enzyme functions as a proton pump across the outside mitochondrial membrane. Depending on metabolic conditions, the enzyme may be involved in NADPH generation for detoxification of peroxides and free radicals and protection from ischemic damage. Hence, given current views on the importance of oxidative stress/damage in aging, this decline in gene expression may be highly important.

B. Genes Upregulated in Five of the Six Tissues.

Several genes were either upregulated or downregulated in five of the six tissues studied. Specifically, 8 genes were upregulated in 5 of 6 tissues. These included four members of the complement pathway and Ceruloplasmin (which encodes a copper-binding protein that may act as a physiological antioxidant).

Complement C3 (K02782), Complement C1Qα (X5886), Complement C1Qc (X66295) Complement C1Qb (M22531): Genes encoding four components of the complement cascade: The clustering of upregulated complement genes is striking and highly significant. The classical complement pathway plays a central role in antibody-mediated cell toxicity. New studies suggest that the role of the pathway is not limited to antibody-mediated reactions. Complement-mediated tissue damage contributes to the myocardial injury associated with ischemia-reperfusion, and in brain injury subsequent to stroke. Augmented membrane attack complex formation through complement activation and assembly has been observed in irreversibly injured myocytes during reperfusion. There is evidence that inhibitors of complement activation attenuate myocardial reperfusion injury (Murohara, et al., 1995; Kirschfink, 1997) and stroke (Huang, et al., 1999) in vivo. Although it was assumed that complement components are deposited from the plasma, resulting in membrane attack complex formation and, ultimately, cell lysis, it is now established that several tissues, including the heart and brain, can synthesize complement components locally. To our knowledge, and based on literature searches, our results provide the first direct evidence that activation of genes encoding several components of the complement pathway is a shared event in the aging process among multiple tissues. Given the ability of complement components to induce cell death, complement induction may be an underlying factor in age-related diseases such as Alzheimer's disease, Parkinson's disease and heart failure.

Ceruloplasmin (U49430): Ceruloplasmin is a blue, copper-binding (6–7 atoms per molecule) glycoprotein found in plasma. Four possible functions are ferroxidase activity, amine oxidase activity, copper transport and homeostasis, and superoxide dismutase activity. These represent an impressive range of functions with the potential to exert a strong influence on pathophysiological changes associated with the aging process in multiple tissues.

Mama (X67809): This molecule is also known as peptidylprolyl isomerase C-associated protein (AF065438), pancreas cancer-associated protein and galectin 6 binding protein. This gene encodes an mRNA that is increased very strongly by adherence and moderately by exposure to tumor necrosis factor and interferon-gamma. The nucleotide sequence extends for 2168 bases and encodes a protein of 559 amino acids with six potential glycosylation sites. The first 100 NH2-terminal amino acids represent a single scavenger receptor cysteine-rich domain. Mama is a normally produced in a variety of tissues and down-modulates endotoxin and proinflammatory responses in vivo (Trahey and Weissman, 1999).

LRG-21 (U19118): This gene encodes a transcription factor known to be upregulated in stress responses.

Serine protease inhibitor 2-2 (M64086) (also known as contrapsin-like protease inhibitor 6). This gene encodes a protein that inhibits trypsin, but not chymotrypsin or elastase. It is induced by acute inflammation and belongs to the serpin family.

C. Genes Downregulated in Five of the Six Tissues.

CD1d1 antigen (M63695): This gene encodes the mouse homolog to human CD1. It is a nonpolymorphic nonclassical main histocompatibility complex (MHC) class I-like molecule encoded outside the MHC.

MAP kinase kinase 6 (U39066): This gene is also known as (mapkk 6) (mapk/erk kinase 6) (sapkk3) and appears to function in mediating stress responses.

HIRA protein (X92590): This gene is a HIRA, a DiGeorge syndrome candidate gene (Farrell, et al., 1999). DiGeorge syndrome is a congenital disease characterized by defects in organs and tissues that depend on contributions by cell populations derived from neural crest for proper development. HIRA could play a part in mechanisms of transcriptional regulation similar to that played by yeast hir1 and hir2 together.

Acetylcholinesterase precursor (X56518): This gene encodes a protein that rapidly hydrolyzes choline released into the synapse. The catalytic activity is acetylcholine+ $H_2O \rightarrow$ choline+acetate. Thus, changes in the expression of this gene have the potential to markedly influence neural transmission.

ZFP-1 (X16493): Belongs to the Krueppel family of c2h2-type zinc-finger proteins which are highly conserved in evolution. The protein encoded by this gene may be involved in transcriptional regulation.

Unknown (AA182189): No significant homology to any gene exists on the public database.

D. Genes Upregulated in the Four Post-Mitotic Tissues Examined (Gastrocnemius, Heart, Cerebellum and Neocortex).

Three such genes were discovered.

Gut-enriched Kruppel-like factor (U20344): May act as a transcriptional activator. Binds the CACC core sequence. May be involved in the differentiation of epithelial cells and may also function in the development of the skeleton and kidney. Belongs to the Kruppel family of C2H2-type zinc-finger proteins.

Galectin-3 (90% homology) (X16834): Galactose-specific lectin which binds IgE. The c-terminal domain belongs to the galaptin (S-lectin) family. Galectin-3 appears to play a role in the endocytosis of both advanced glycation end products (which are widely thought to be involved in the aging process) and modified low density lipoproteins (involved in atherosclerosis) (Zhu, et al., 2001).

Apolipoprotein D (X82648): Apolipoprotein D (apoD) is a 29-kDa glycoprotein that is primarily associated with high density lipoproteins in human plasma (reviewed in Rassart, et al., 2000). It is an atypical apolipoprotein and, based on its primary structure, apoD is predicted to be a member of the lipocalin family. The physiological ligand for apoD is unclear. ApoD is present at high concentrations at sites of regenerating peripheral nerves and in the cerebrospinal fluid of patients with neurodegenerative conditions, such as Alzheimer's disease. While its role in metabolism has yet to be defined, apoD is likely to be a multi-ligand, multi-functional transporter.

E. Genes Downregulated in the Four Post-Mitotic Tissues Examined (Gastrocnemius, Heart, Cerebellum and Neocortex).

Four such genes were discovered.

Acrosin (80% identical) (D00754): Acrosin is the major protease of mammalian spermatozoa. It is a serine protease of trypsin-like cleavage specificity which is synthesized in a zymogen form, proacrosin and stored in the acrosome. Little is known about its functions in cells other than spermatozoa.

Cytokeratin 15 homolog (56% identity) (D16313): Little is known about this molecule. Cytokeratin 15 may be preferentially expressed in epithelial stem cells (Lyle, et al., 1999).

Integral Membrane Protein 2A (Itm2A, 96% identity) (L38971): This gene encodes a type II membrane protein. It is expressed in mandibular condyles, in bone and in hair follicles. Strong expression is seen in osteogenic tissues, such as neonatal calvaria, paws, tail and skin.

Retinoic Acid-Binding Protein 1 (CRABP-1) (X15789): Cytosolic CRABPs may regulate the access of retinoic acid to the nuclear retinoic acid receptors. It belongs to the fabp/p2/crbp/crabp family of transporter. It has recently been discovered that this protein is associated with mitochondria (Ruff and Ong, 2000).

Conclusion.

To our knowledge, the genes described in this application provide the first genetic evidence for common gene expression alterations involved in aging. An upregulation of genes involved in inflammatory processes is obvious, providing novel targets for genetic and pharmacological interventions. Genes that decrease in expression with aging may underlie age-associated defects that could also be corrected by specific interventions, such as gene therapy. Importantly, by identifying these genes, we have identified specific targets for intervention in aging and associated diseases.

REFERENCES

Ausabel, et al., (eds.), "Current Protocols in Molecular Biology," John Wiley & Sons, NY, 1991.
Barnay, *Proc. Natl. Acad. Sci. USA* 88:189–93, 1991
Cross, M., Mangelsdorf, I., Wedel, A., Renkawitz, R., "Mouse lysozyme M gene: isolation, characterization and expression studies," *Proc. Natl. Acad. Sci. USA* 85(17): 6232–6, 1988.
Drysdale, B. E., Howard, D. L. and Johnson, R. J., "Identification of a lipopolysaccharide inducible transcription factor in murine macrophages," *Mol. Immunol.* 33:939–998, 1996.
Farrell, M. J., Stadt, H., Wallis, K. T., Scambler, P., Hixon, R. L., Wolfe, R., Leatherbury, L., Kirby, M. L., "HIRA, a DiGeorge syndrome candidate gene, is required for cardiac outflow tract septation.
Huang, J., Kim, L. J., Mealey, R., Marsh, H. C., Jr., Zhang, Y., Tenner, A. J., Connolly, E. S., Jr, Pinsky, D. J., "Neuronal protection in stroke by an sLex-glycosylated complement inhibitory protein," *Science* 285(5427):595–9, 1999.
Kirschfink, M., "Controlling the complement system in inflammation. *Immunopharmacology* 38:51–62, 1997.
Lopez-Boado, et al., *J. Biol. Chem.* 271:32105, 1996
Lyle, S., Christofidou-Solomidou, M., Liu, Y., Elder, D. E., Albelda, S., Cotsarelis, G. J., "Human hair follicle bulge cells are biochemically distinct and possess an epithelial stem cell phenotype," *Investig. Dermatol. Symp. Proc.* 4(3):296–301, 1999.
Murohara, T., J. P. Guo, J. A. Delyani, and A. M. Lefer, "Cardioprotective effects of selective inhibition of the two complement activation pathways in myocardial ischemia and reperfusion injury," *Meth. Find. Exp. Clin. Pharmacol.* 17:449–507, 1995.
Pugh, T. D., Klopp, R. G.,and Weindruch, R., "Controlling caloric consuption: Protocols for rodents and rhesus monkeys," *Neurobiol. Aging* 20:157–165, 1999.
Rassart, E., Bedirian, A., Do, Carmo, S., Guinard, O., Sirois, J., Terrisse, L., Milne, R., "Apolipoprotein D," *Biochim. Biophys. Acta* 1482(1–2):185–98, 2000.
Ruff, S. J. and Ong, D. E., "Cellular retinoic acid binding protein is associated with mitochondria," *FEBS Lett.* 487(2):282–286, 2000.
Trahey and Weissman, "Cyclophilin C-associated protein: a normal secreted glycoprotein that down-modulates endotoxin and proinflammatory responses in vivo," *Circ. Res.* 84(2):127–35, 1999.
Zhu, W., Sano, H., Nagai, R., Fukuhara, K., Miyazaki, A., Horiuchi, S., "The Role of Galectin-3 in Endocytosis of Advanced Glycation End Products and Modified Low Density Lipoproteins," *Biochem. Biophys. Res. Commun.* 280(4):1183–1188, 2000.

TABLE 2

Shared Age-Associated Changes in Gene Expression Among Four-to-Six Tissues
Six tissues were studied: cerebellum, neocortex, gastrocnemium, heart, kidney and liver. The changes listed for four tissues were confined to those shared among the four post-mitotic tissue analyzed (heart, cerebellum, neocortex and gastrocnemius). The data for each tissue represent the fold change with aging and the standard error for the nine pair-wise comparisons (see "Methods").

| ORF | Gene | Cerebellum | Neocortex | Gasteroc. | Heart | Kidney | Liver |
|---|---|---|---|---|---|---|---|
| *Up in 6 of 6 tissues* | | | | | | | |
| M21050 | Lysozyme M | 2.2 (0.3) | 10.9 (1.3) | 1.8 (0.3) | 1.5 (0.2) | 2.4 (0.4) | 2.3 R (1.3) |
| *Down in 6 of 6 tissues* | | | | | | | |
| Z49204 | NADP Transhydrogenase | −1.4 (0.1) | −1.4 (0.1) | −2.9 (0.4) | −1.4 (0.5) | −2.5 (0.2) | −4.3 (0.5) |
| *Up in 5 of 6 tissues* | | | | | | | |
| U49430 | Ceruloplasmin | | 1.7 (0.8) | 2.1 (0.3) | 3.0 (0.4) | 2.1 (0.3) | 1.9 (1.1) |
| K02782 | Complement C3 | 3.5 (0.9) | 2.3 (0.7) | | 2.0 (0.1) | 11.1 (1.5) | 1.7 (0.7) |
| X58861 | Complement C1Qa | 4.8 (0.5) | 1.7 (0.1) | | 1.5 (0.1) | 7.3 (1.5) | 4.4 (4.0) |
| X66295 | Complement C1Qc | 3.1 (0.4) | 1.4 (0.1) | | 1.5 (0.1) | 1.7 (0.2) | 2.6 (2.0) |
| M22531 | Complement C1Qb | 2.4 (0.1) | 1.9 (0.1) | 1.4 (2.1) | 1.2 (0.5) | 1.6 (0.2) | 1.7 (1.6) |
| X67809 | mama | 24.3 (8.1) | 4.1 (2.9) | | 1.5 (0.6) | 14.0 (3.5) | 1.8 (3.2) |
| U19118 | LRG-21 | 1.5 (1.1) | 2.6 (0.3) | 3.0 (1.0) | 1.3 (0.1) | 1.5 (0.1) | |
| M64086 | Spi2 proteinase | 6.1 (2.7) | 5.6 (1.7) | 4.3 (1.7) | 9.6 (2.5) | | 1.7 (4.6) |
| *Down in 5 of 6 tissues* | | | | | | | |
| M63695 | CD1.1 | | −1.8 (0.3) | −1.4 (1.0) | −3.7 (2.0) | −1.7 (0.2) | −1.3 (0.7) |
| U39066 | MAP kinase kinase | | −2.1 (0.4) | −1.8 (0.2) | −4.5 (1.5) | −1.3 (0.6) | −1.6 (1.4) |
| X92590 | HIRA | | −1.6 (0.1) | −4.8 (1.2) | −7.1 (3.7) | −2.9 (3.4) | −4.3 (1.3) |
| X56518 | Acetylcholinesterase | −2.1 (0.5) | −10.6 (4.7) | −10.1 (3.3) | −8.3 (6.5) | | −4.8 (0.5) |
| AA182189 | Unknown | −1.5 (1.4) | −1.4 (0.6) | −1.7 (0.3) | −2.3 (0.6) | −1.3 (0.7) | |
| X16493 | ZFP-1 | −1.7 (1.9) | −1.2 (0.1) | 1.7 (0.7) | −1.3 (0.1) | | −2.8 (0.5) |
| *Up in 4 Postmitotic Tissues* | | | | | | | |
| U20344 | Kruppel-like Factor 4 | 1.5 (0.2) | 1.8 (0.3) | 2.5 (0.5) | 1.6 (0.2) | | |
| X16834 | Galectin-3 (MAC-2) | 2.2 (0.8) | 1.6 (0.8) | 6.0 (1.5) | 5.2 (2.7) | | |
| X82648 | Apolipoprotein D | 1.5 (0.1) | 2.2 (0.1) | 2.6 (0.4) | 8.3 (2.1) | | |

TABLE 2-continued

Shared Age-Associated Changes in Gene Expression Among Four-to-Six Tissues
Six tissues were studied: cerebellum, neocortex, gastrocnemium, heart, kidney and liver. The changes listed for four tissues were confined to those shared among the four post-mitotic tissue analyzed (heart, cerebellum, neocortex and gastrocnemius). The data for each tissue represent the fold change with aging and the standard error for the nine pair-wise comparisons (see "Methods").

| ORF | Gene | Cerebellum | Neocortex | Gasteroc. | Heart | Kidney | Liver |
|---|---|---|---|---|---|---|---|
| | | Down in 4 Postmitotic Tissues | | | | | |
| D00754 | Acrosin | −3.0 (2.0) | −5.7 (3.3) | −4.2 (2.5) | −5.1 (2.0) | | |
| D16313 | Cytokeratin 15 | −1.6 (1.1) | −4.9 (1.5) | −3.9 (1.2) | −4.2 (2.2) | | |
| L38971 | Integral Membrane Protein 2A | −1.7 (0.1) | −1.4 (0.1) | −1.7 (0.2) | −2.9 (1.1) | | |
| X15789 | CRABP-1 | −1.7 (1.3) | −2.7 (0.4) | −1.7 (0.3) | −1.8 (0.8) | | |

We claim:

1. A method for screening a compound for the ability to inhibit expression pattern of biomarker sequences that are differentially expressed with age in mice comprising the steps of:
    (a) dividing test mice into first and second groups;
    (b) exposing the first group to a test compound;
    (c) analyzing samples of the first and second groups for the expression pattern of biomarker sequences M21050 (SEQ ID NO: 1), U49430 (SEQ ID NO: 2), K02782 (SEQ ID NO: 3), X66295 (SEQ ID NO: 4), and X82648 (SEQ ID NO: 5); and
    (d) comparing the analysis of the first and second groups and identifying test compounds that inhibit the expression pattern of the biomarker sequences of said analyzing step (c) in the first group such that the expression patterns are decreased relative to the second group and thus more similar to those observed in biologically younger animals.

2. The method of claim 1 wherein the sample comprises an organ, tissue or cell.

3. The method of claim 1 wherein said analyzing step (c) comprises detecting RNA or cDNA encoded by the biomarker sequences listed in said analyzing step (c).

4. The method of claim 1 wherein said analyzing step (c) comprises detecting protein encoded by the biomarker sequences listed in said analyzing step (c).

5. The method of in claim 2, wherein the tissue is selected from the group consisting of cerebullum, neocortex, heart tissue, skeletal muscle, liver and kidney tissue.

* * * * *